United States Patent
Hara et al.

(10) Patent No.: US 9,226,713 B2
(45) Date of Patent: Jan. 5, 2016

(54) INFORMATION PROCESSING METHOD, APPARATUS, AND PROGRAM

(75) Inventors: Masahiro Hara, Kawasaki (JP); Kazuho Maeda, Kawasaki (JP); Yoshinori Yaginuma, Kawasaki (JP)

(73) Assignee: FUJITSU LIMITED, Kawasaki (JP)

( * ) Notice: Subject to any disclaimer, the term of this patent is extended or adjusted under 35 U.S.C. 154(b) by 1103 days.

(21) Appl. No.: 13/226,549

(22) Filed: Sep. 7, 2011

(65) Prior Publication Data

US 2012/0065915 A1    Mar. 15, 2012

(30) Foreign Application Priority Data

Sep. 13, 2010  (JP) .................................. 2010-204402

(51) Int. Cl.
| | |
|---|---|
| G01C 21/10 | (2006.01) |
| A61B 5/00 | (2006.01) |
| G01P 7/00 | (2006.01) |
| G01M 1/12 | (2006.01) |
| A61B 5/11 | (2006.01) |
| G06F 19/00 | (2011.01) |

(52) U.S. Cl.
CPC ............. *A61B 5/7221* (2013.01); *A61B 5/1121* (2013.01); *G01M 1/122* (2013.01); *G01P 7/00* (2013.01); *A61B 2562/0219* (2013.01); *G06F 19/3481* (2013.01)

(58) Field of Classification Search
CPC ........... G01M 1/122; G01C 21/16; G01P 7/00
USPC .......................................... 702/141, 160, 169
See application file for complete search history.

(56) References Cited

U.S. PATENT DOCUMENTS

| | | | |
|---|---|---|---|
| 6,539,336 B1 * | 3/2003 | Vock et al. ..................... | 702/182 |
| 7,031,872 B2 | 4/2006 | Tanaka et al. | |

(Continued)

FOREIGN PATENT DOCUMENTS

| | | | |
|---|---|---|---|
| JP | 2007199173 A | * | 8/2007 |
| JP | 2008-73267 A | | 4/2008 |

(Continued)

OTHER PUBLICATIONS

Jessa, Tega, What is Hooke's Law, http://www.universetoday.com/55027/hookes-law, Feb. 10, 2010.*

(Continued)

*Primary Examiner* — Timothy H Hwang
(74) *Attorney, Agent, or Firm* — Oblon, McClelland, Maier & Neustadt, L.L.P.

(57) ABSTRACT

A method executed by a computer includes applying a correction to an acceleration value of an object at an interval; calculating an initial speed of the object by assigning the corrected acceleration value in a period to a third relational expression that is obtained by transforming a first relational expression and a second relational expression so as to obtain an initial speed from the acceleration in the period and the interval, where the first relational expression is to obtain an object position from acceleration and an initial speed, and the second relational expression represents force applied to the object due to fluctuation of the center of gravity of the object as a motion equation of a spring model; and calculating coordinate values over a horizontal plane that indicates a center of gravity of the object by assigning the corrected acceleration value and the initial speed to the first relational expression.

10 Claims, 35 Drawing Sheets

(56) References Cited

U.S. PATENT DOCUMENTS

| | | | |
|---|---|---|---|
| 7,057,551 B1* | 6/2006 | Vogt | 342/357.57 |
| 7,366,612 B2* | 4/2008 | Yang et al. | 701/504 |
| 7,712,365 B1* | 5/2010 | James | 73/488 |
| 7,725,289 B2* | 5/2010 | Nagashima et al. | 702/160 |
| 2007/0073514 A1* | 3/2007 | Nogimori et al. | 702/160 |
| 2007/0265770 A1* | 11/2007 | Hirose | 701/202 |
| 2008/0281234 A1* | 11/2008 | Goris et al. | 600/595 |
| 2009/0069724 A1* | 3/2009 | Otto et al. | 600/595 |
| 2011/0032105 A1* | 2/2011 | Hoffman et al. | 340/573.1 |
| 2011/0160996 A1* | 6/2011 | Terai et al. | 701/200 |
| 2011/0166488 A1* | 7/2011 | Miyake | 601/34 |
| 2012/0303319 A1* | 11/2012 | Kirkeby | 702/160 |

FOREIGN PATENT DOCUMENTS

| | | |
|---|---|---|
| JP | 2008-229266 A | 10/2008 |
| WO | WO-2004/014230 | 2/2004 |

OTHER PUBLICATIONS

Acceleration, Velocity, and Position, http://www.ugrad.math.ubc.ca/coursedoc/math101/notes/applications/velocity.html, available online on Aug. 19, 2010.*

* cited by examiner

FIG. 3

| TIME | x-AXIS ACCELERATION | y-AXIS ACCELERATION | z-AXIS ACCELERATION |
|---|---|---|---|
| 10:30:46.002 | −906 | −221 | 401 |
| 10:30:46.007 | −902 | −235 | 398 |
| 10:30:46.012 | −905 | −245 | 404 |
| 10:30:46.017 | −905 | −254 | 416 |
| 10:30:46.022 | −888 | −260 | 407 |
| 10:30:46.027 | −891 | −263 | 407 |
| 10:30:46.032 | −881 | −269 | 404 |
| ... | ... | ... | ... |

FIG. 4

| PARAMETER | VALUE |
|---|---|
| XFullScale | 1.026 |
| XOffset | 0.015 |
| YFullScale | ... |
| YOffset | ... |
| ZFullScale | ... |
| ZOffset | ... |

FIG. 5

| TIME | BEFORE OFFSET CORRECTION ||| AFTER OFFSET CORRECTION |||
|---|---|---|---|---|---|---|
| | x-AXIS ACCELERATION | y-AXIS ACCELERATION | z-AXIS ACCELERATION | x-AXIS ACCELERATION | y-AXIS ACCELERATION | z-AXIS ACCELERATION |
| 10:30:46.002 | −906 | −221 | 401 | −883.056 | −215.415 | 390.8232 |
| 10:30:46.007 | −902 | −235 | 398 | −879.157 | −229.06 | 387.8992 |
| 10:30:46.012 | −908 | −245 | 404 | −882.081 | −238.806 | 393.7472 |
| ... | ... | ... | ... | ... | ... | ... |

FIG. 7

| INTERVAL | START TIME | END TIME | GAIT CYCLE Tw | WALKING FLAG | COMPLETION FLAG |
|---|---|---|---|---|---|
| 1 | $TM_1$ | $TM_2$ | $(TM_2-TM_1)$ | 1 | 1 |
| 2 | $TM_2$ | $TM_3$ | $(TM_3-TM_2)$ | 1 | 1 |
| ... | ... | ... | ... | | |

FIG. 18

| PERIOD | VALUE OF K (MOVING DIRECTION) | VALUE OF K (RIGHT AND LEFT DIRECTION) |
|---|---|---|
| $T_1$ | ... | ... |
| $T_2$ | ... | ... |
| ... | ... | ... |

FIG. 19

| PERIOD | INITIAL SPEED (MOVING DIRECTION) | INITIAL SPEED (RIGHT AND LEFT DIRECTION) |
|---|---|---|
| $T_1$ | . . . | . . . |
| $T_2$ | . . . | . . . |
| . . . | . . . | . . . |

FIG. 20

| TIME | POSITION (y-AXIS) | POSITION (z-AXIS) |
|---|---|---|
| 10:31:01.992 | −0.000001 | 0.000011 |
| 10:31:01.997 | −0.000001 | 0.000023 |
| 10:31:02.002 | −0.000002 | 0.000034 |
| 10:31:02.007 | −0.000002 | 0.000045 |
| 10:31:02.012 | −0.000003 | 0.000056 |
| 10:31:02.017 | −0.000003 | 0.000066 |
| 10:31:02.022 | −0.000004 | 0.000077 |
| 10:31:02.027 | −0.000004 | 0.000088 |
| 10:31:02.032 | −0.000003 | 0.000099 |
| 10:31:02.037 | −0.000002 | 0.000109 |
| 10:31:02.042 | −0.000001 | 0.000120 |
| ... | ... | ... |

FIG. 23

| TIME | POSITION (y-AXIS) | POSITION (z-AXIS) | RELATIVE POSITION (y-AXIS) | RELATIVE POSITION (z-AXIS) |
|---|---|---|---|---|
| 10:31:01.992 | −0.000001 | 0.000011 | −0.000077 | 0.000103 |
| 10:31:01.997 | −0.000001 | 0.000023 | −0.000077 | 0.000114 |
| 10:31:02.002 | −0.000002 | 0.000034 | −0.000078 | 0.000125 |
| 10:31:02.007 | −0.000002 | 0.000045 | −0.000079 | 0.000136 |
| 10:31:02.012 | −0.000003 | 0.000056 | −0.000079 | 0.000147 |
| 10:31:02.017 | −0.000003 | 0.000066 | −0.000080 | 0.000158 |
| 10:31:02.022 | −0.000004 | 0.000077 | −0.000080 | 0.000169 |
| 10:31:02.027 | −0.000004 | 0.000088 | −0.000080 | 0.000179 |
| 10:31:02.032 | −0.000003 | 0.000099 | −0.000079 | 0.000190 |
| 10:31:02.037 | −0.000002 | 0.000109 | −0.000078 | 0.000201 |
| 10:31:02.042 | −0.000001 | 0.000120 | −0.000077 | 0.000211 |

FIG. 25

| REGION RANGE | REGION NUMBER | COORDINATE VALUES | DISTANCE |
|---|---|---|---|
| −180°~−177° | 0 | $(y_0, z_0)$ | 0.001192 |
| −177°~−174° | 1 | $(y_1, z_1)$ | 0.001225 |
| −174°~−171° | 2 | $(y_2, z_2)$ | 0.001205 |
| −171°~−168° | 3 | $(y_3, z_3)$ | 0.001050 |
| −168°~−165° | 4 | $(y_4, z_4)$ | 0.000883 |
| ... | ... | ... | ... |
| 0°~3° | 60 | $(y_{60}, z_{60})$ | 0.001037 |
| ... | ... | ... | ... |
| 177°~−180° | 119 | $(y_{119}, z_{119})$ | 0.001277 |

FIG. 26

| REGION RANGE | REGION NUMBER | NORMAL CONDITION | FATIGUE CONDITION |
|---|---|---|---|
| −180°~−177° | 0 | 0.001278 | 0.036072 |
| −177°~−174° | 1 | 0.001273 | 0.034539 |
| −174°~−171° | 2 | 0.001200 | 0.033003 |
| −171°~−168° | 3 | 0.001069 | 0.031504 |
| −168°~−165° | 4 | 0.000886 | 0.030783 |
| ... | ... | ... | ... |
| 0°~3° | 60 | 0.001049 | 0.037567 |
| ... | ... | ... | ... |
| 177°~−180° | 119 | 0.001268 | 0.038296 |

FIG. 28

| PHYSICAL CONDITION HISTORY |
|---|
| PHYSICAL CONDITION A |
| PHYSICAL CONDITION A |
| PHYSICAL CONDITION B |
| PHYSICAL CONDITION B |
| PHYSICAL CONDITION B |
| PHYSICAL CONDITION B |

FIG. 29

| CURRENT PHYSICAL CONDITION | RESET FLAG |
|---|---|
| PHYSICAL CONDITION B | OFF |

INFORMATION PROCESSING METHOD, APPARATUS, AND PROGRAM

CROSS-REFERENCE TO RELATED APPLICATION

This application is based upon and claims the benefit of priority of the prior Japanese Patent Application No. 2010-204402 filed on Sep. 13, 2010, the entire contents of which are incorporated herein by reference.

FIELD

The embodiments discussed herein are related to an information processing method, apparatus and program for analyzing fluctuation of the center of gravity.

BACKGROUND

Human beings balance one's body while standing by almost always positioning oneself by refined body movements (referred to as fluctuation of the center of gravity). Conventionally, a test has been conducted to check fluctuation of the center of gravity by using a stabilometer to find how much a body fluctuates based on the measured result. The stabilometer measures fluctuation of the center of gravity when a body is on the stabilometer.

Moreover, conventionally, there has been a technique to estimate fluctuation of the center of gravity by using an acceleration sensor. According to the technique, a position at a measurement is obtained by applying a double integration to an acceleration value measured by the acceleration sensor to estimate a fluctuation of the center of gravity. When a double integration is applied to an acceleration value, an integration constant such as an initial position and an initial speed is provided. However, according to the technique, a calculation is conducted by assuming an initial position and an initial speed as 0. In other words, in the technique, a measurement is assumed to be started under a standstill state.

Related-art techniques are disclosed in WO2004/014230, Japanese Laid-open Patent Publication Nos. 2008-229266 and 2008-073267.

SUMMARY

According to an aspect of an embodiment, an information processing method executed by a computer includes receiving an acceleration value, measured by an acceleration sensor, of an object at a sampling interval; applying a correction to the received acceleration value and storing the corrected acceleration value in a data storage unit; calculating an initial speed of the object by inputting the corrected acceleration value of a period to a third relational expression which is obtained by transforming a first relational expression and a second relational expression so as to obtain the initial speed from the corrected acceleration in the period and the certain interval, the first relational expression obtaining a position of the object from corrected acceleration and the initial speed, and the second relational expression representing a force applied to the object due to a change of a center of gravity of the object as a motion equation of a spring model and storing the calculated initial speed in a storage device; and calculating coordinate values over a horizontal plane that indicates a center of gravity of the object by inputting the corrected acceleration value and the calculated initial speed to the first relational expression and storing the calculated coordinate values in the storage device.

The object and advantages of the invention will be realized and attained at least by the elements, features, and combinations particularly pointed out in the claims.

It is to be understood that both the foregoing general description and the following detailed description are exemplary and explanatory and are not restrictive of the invention, as claimed.

BRIEF DESCRIPTION OF DRAWINGS

FIG. 3 illustrates an example of data stored in a measurement result storage unit;

FIG. 4 illustrates an example of data stored in a parameter storage unit;

FIG. 5 illustrates acceleration before and after applying offset corrections;

FIG. 7 illustrates an example of data stored in an interval data storage unit;

FIG. 18 illustrates an example of data stored in a variable storage unit;

FIG. 19 illustrates an example of data stored in an initial speed storage unit;

FIG. 20 illustrates an example of data stored in a center of gravity fluctuation storage unit;

FIG. 23 illustrates data that is converted to a relative position by assuming a center of displacement "d" as an original point;

FIG. 25 illustrates data of the first point;

FIG. 26 illustrates an example of data stored in a physical condition database (DB);

FIG. 28 illustrates an example of physical condition history data stored in a physical condition history data storage unit;

FIG. 29 illustrates an example of physical condition management data stored in a physical condition history data storage unit;

DESCRIPTION OF EMBODIMENTS

Figure 1:
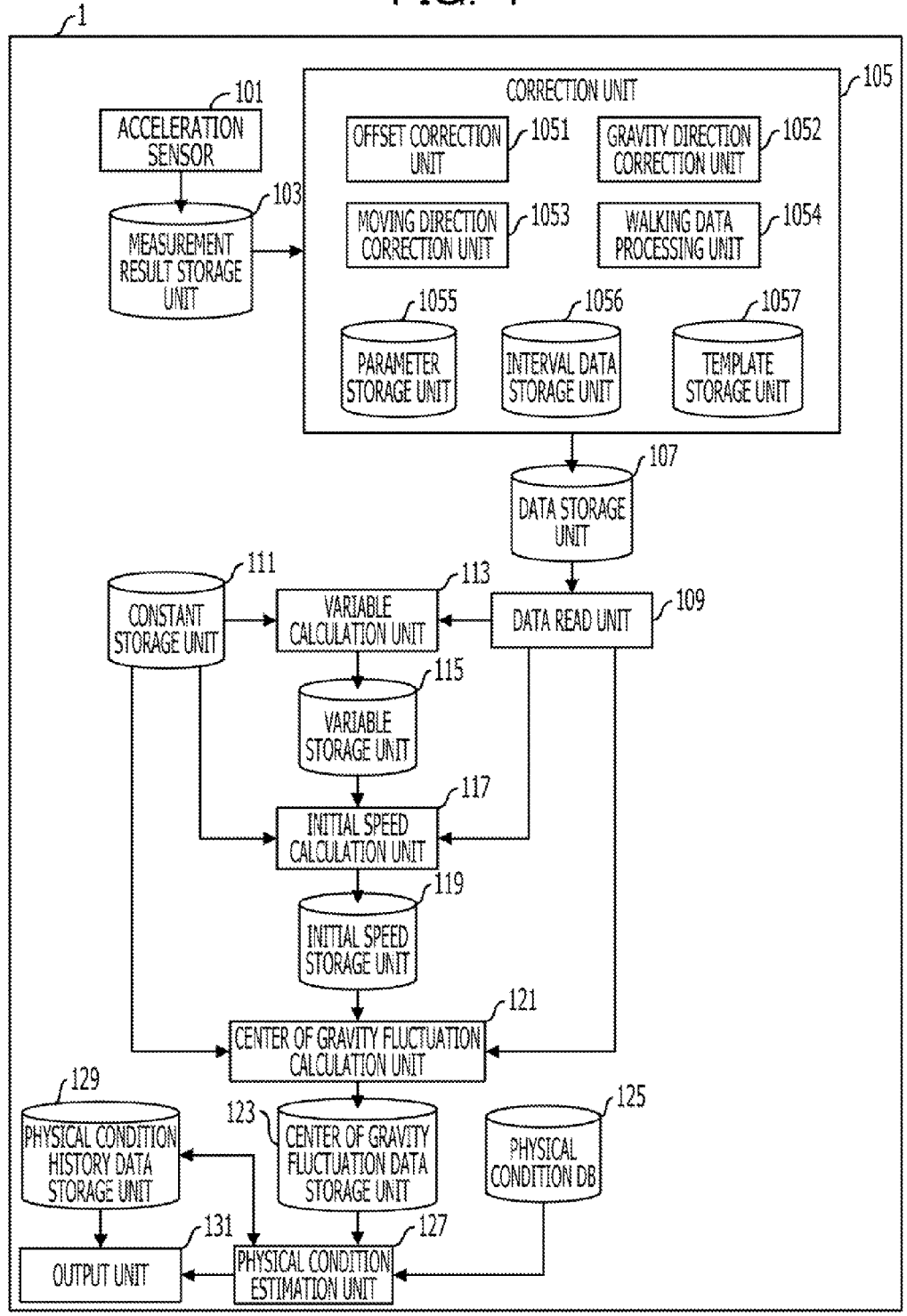
FIG. 1 is a functional block diagram of a mobile terminal according to a first embodiment.

According to the above related-art techniques, an error may be caused in estimating the fluctuation of the center of gravity when a measurement starts under a state in which a person is not completely still. Furthermore, fluctuation of the center of gravity may not be estimated, for example, when a person is moving.

According to an embodiment, fluctuation of the center of gravity of a subject is estimated with high accuracy by applying a spring model by focusing on characteristics of the fluctuation of the center of gravity in which force acts to return the center of gravity to a virtual true center position in spring model.

For example, a force (F) that acts on a body by fluctuation of the center of gravity is expressed by a relational expression (1) as illustrated below when the force is represented by equation of motion of a spring model using the characteristics as shown below:

1. A force (F) that acts on a body by fluctuation of the center of gravity is directed to a true center point (C).
2. A force (F) that acts on a body by fluctuation of the center of gravity is proportional to a distance from a true center point (C).

$$F = m^* a_t = -k^*(x_t - C) \tag{1}$$

where, "m" indicates mass, "$a_t$" indicates acceleration, "k" indicates a spring constant in the spring model, and "$x_t$" indicates a position of the center of gravity. Note that "t" is an integer from 0 to N−1, while N indicates the number of samples of acceleration.

A position of the body may be calculated by applying a double integral of acceleration. A relationship between acceleration and a position of the body may be represented by the expression below because acceleration "at" and a position "xt" are discrete values.

Expression 2

$$x_t = \sum_{j=0}^{t} \left( \sum_{i=0}^{j} a_i \Delta t + v_0 \right) \times \Delta t + x_0 \tag{2}$$

Here, "$\Delta t$" indicates a sampling interval, "$v_0$" indicates an initial speed, and "$x_0$" indicates an initial position.

When a subscript in the expression (2) is changed to "t−1", the following expression is obtained.

Expression 3

$$x_{t-1} = \sum_{j=0}^{t-1} \left( \sum_{i=0}^{j} a_i \Delta t + v_0 \right) \times \Delta t + x_0 \tag{3}$$

When "xt−xt−1" is represented by the expressions (2) and (3), the following expression is obtained.

Expression 4

$$x_t - x_{t-1} = \sum_{i=0}^{t} a_i \times \Delta t^2 + v_0 \times \Delta t \tag{4}$$

When an auto-regression model is applied to the expression (1), the expression (1) is transformed to the following expression (5):

Expression 5:

$$a_t = -k/m^* x_{t-1} + w_t \tag{5}$$

where "wt" is an error term.

When the subscript of Expression 5 is changed to "t−1", the following expression is obtained.

$$a_{t-1} = -k/m^* x_{t-2} + w_{t-1} \tag{6}$$

When "$a_t - a_{t-1}$" is represented by the expressions (5) and (6), the following expression is obtained.

Expression 7

$$a_t - a_{t-1} = -(x_{t-1} - x_{t-2}) + w_t - w_{t-1} \tag{7}$$

When the expression 4 is assigned to the expression (7), the following expression (8) is obtained.

Expression (8)

$$a_t - a_{t-1} = -\frac{k}{m} \times \left\{ \sum_{i=0}^{t-1} a_i \times \Delta t^2 + v_0 \times \Delta t \right\} + w_t - w_{t-1} \tag{8}$$

The expression (8) is transformed as below.

$$a_t = a_{t-1} - \frac{k}{m} \times \Delta t^2 \times \left\{ \sum_{i=0}^{t-1} a_i \right\} - \frac{k}{m} \times \Delta t \times v_0 + w_t - w_{t-1}$$

Expression 9

$$a_t = \left(1 - \frac{k}{m} \times \Delta t^2\right) a_{t-1} - \frac{k}{m} \times \Delta t^2 \times \left\{ \sum_{i=0}^{t-2} a_i \right\} - \frac{k}{m} \times \Delta t \times v_0 + w_t - w_{t-1} \tag{9}$$

When the subscript of expression (9) is changed to "t−1", the following expression is obtained.

Expression (10)

$$a_{t-1} = \left(1 - \frac{k}{m} \times \Delta t^2\right) a_{t-2} - \frac{k}{m} \times \Delta t^2 \times \left\{\sum_{i=0}^{t-3} a_i\right\} - \frac{k}{m} \times \Delta t \times v_0 + w_{t-1} - w_{t-2} \quad (10)$$

When "$a_t - a_{t-1}$" is represented by the expressions (9) and (10), the following expression is obtained.

Expression (11)

$$a_t - a_{t-1} = \left(1 - \frac{k}{m} \times \Delta t^2\right)(a_{t-1} - a_{t-2}) - \frac{k}{m} \times \Delta t^2 \times a_{t-2} + w_t - 2w_{t-1} + w_{t-2} \quad (11)$$

The expression (11) is transformed as below.

$$at = (2 - k/m \ast \Delta t^2) - a_{t-2} + w_t - 2w_{t-1} + w_{t-2} \quad (12)$$

Here, variable K=k/m*Δt2, and an error term is Wt=wt−2wt−1+wt−2, the expression 12 is transformed as follows.

$$at = (2 - K) \ast a_{t-1} - a_{t-2} + w_t \quad (13)$$

When the least squares method is applied to the expression (13), the following expression is derived.

Expression 14

$$\sum_{i=2}^{N} \{a_i - (2 - K)a_{i-1} + a_{i-2}\}^2 \quad (14)$$

Moreover, the expression (14) is transformed as follows.

Expression (15)

$$\sum_{i=2}^{N} \{(2 - K)a_i^2 - 4(2 - K)a_i a_{i-1} + 2a_i^2 + 2a_i a_{i-2}\} \quad (15)$$

Variables, $A_0$, $A_1$, $A_2$, and Y are defined as follows:

$$A_0 = \sum_{i=2}^{N-1} a_i^2, \quad A_1 = \sum_{i=2}^{N-1} a_i a_{i+1}, \quad A_2 = \sum_{i=2}^{N-1} a_i a_{i-2}, \quad Y = 2 - K$$

When the expression (15) is obtained by variables A0, A1, A2, and Y, the following expression (16) is obtained.

$$A_0 Y^2 - 4A_1 Y + 2A_0 + 2A_2 \quad (16)$$

When the expression (16) is differentiated partially by Y, "$2A_0 Y - 4A_1$" is obtained, and assumed to be "$2A_0 Y - 4A_1$" here. Then, "$Y = 2A_1/A_0$" is obtained and the variable "K" is defined as follows.

Expression 17

$$K = 2\left(1 - \frac{\sum_{i=2}^{N-1} a_i a_{i-1}}{\sum_{i=2}^{N-1} a_i^2}\right) \quad (17)$$

Meanwhile, when the expression (2) is assigned to the expression (5), the following expression is obtained.

Expression 18

$$a_t = -\frac{k}{m} \times \left[\sum_{j=0}^{t-1}\left\{\sum_{i=0}^{j} a_i \Delta t^2 + v_0 \Delta t\right\} + x_0\right] + y_t \quad (18)$$

When the subscript of the expression 18 is changed to "t−1", the following expression is obtained.

Expression 19

$$a_{t-1} = -\frac{k}{m} \times \left[\sum_{j=0}^{t-2}\left\{\sum_{i=0}^{j} a_i \Delta t^2 + v_0 \Delta t\right\} + x_0\right] + y_{t-1} \quad (19)$$

When "$a_t - a_{t-1}$" is represented by the expressions (18) and (19), the following expression is obtained.

Expression 20

$$a_t - a_{t-1} = -\frac{k}{m} \times \left\{\sum_{i=0}^{t-1} a_i \Delta t^2 + v_0 \Delta t\right\} + y_t - y_{t-1} \quad (20)$$

The expression (20) is transformed as below.

Expression (21)

$$a_t = \left(1 - \frac{k}{m}\Delta t^2\right) \times a_{t-1} - \frac{k}{m}\Delta t^2 \times \sum_{i=0}^{t-2} a_i - \frac{k}{m}\Delta t^2 \times v_0 + y_t - y_{t-1} \quad (21)$$

Here, variable K=k/m*Δt², and an error term is "$Y_t = y_t - y_{t-1}$," the expression (21) is transformed as below.

Expression (22)

$$a_t = (1 - K)a_{t-1} - K \times \sum_{i=0}^{t-2} a_i - \frac{K}{\Delta t} v_0 + Y_i \quad (22)$$

When the least squares method is applied to the expression (22), the following expression is derived.

Expression (23)

$$\sum_{j=2}^{N}\left\{a_j - (1-K)a_{j-1} + K\sum_{i=0}^{j-2} a_i + \frac{K}{\Delta t}v_0\right\}^2 \qquad (23)$$

A variable "Bj" is defined as follows.

$$B_j = a_j - (1-K)a_{j-1} + K\sum_{i=0}^{j-2} a_i$$

When the expression (23) is represented by the variable "$B_j$," the following expression is obtained.

Expression (24)

$$\sum_{j=2}^{N}\left\{B_j + \frac{K}{\Delta t}v_0\right\}^2 \qquad (24)$$

Moreover, the expression (24) is transformed as follows.

Expression (25)

$$\sum_{j=2}^{N} B_j^2 + 2\frac{K}{\Delta t}v_0 \sum_{j=2}^{N} B_j + \frac{K^2}{\Delta t^2}v_0^2 \times (N-2) \qquad (25)$$

When the expression (25) is differentiated partially by $v_0$ and 0 is obtained, the following expression is obtained.

Expression (26)

$$2\frac{K}{\Delta t}\sum_{j=2}^{N} B_j + 2\frac{K^2}{\Delta t^2}v_0(N-2) = 0 \qquad (26)$$

When the expression (26) is transformed so that $v_0$ is obtained, the following expression is obtained.

Expression (27)

$$v_0 = -\frac{\sum_{j=2}^{N} B_j}{K(N-2)} \times \Delta t \qquad (27)$$

When the variable "$B_j$" is returned to the original expression, the following expression is obtained.

Expression (28)

$$v_0 = -\frac{\sum_{j=2}^{N}\left(a_j - (1-K)a_{j-1} + K\left(\sum_{i=0}^{j-2} a_i\right)\right)}{K(N-2)} \times \Delta t \qquad (28)$$

According to the embodiment, a value of the variable K is calculated by assigning the number of N acceleration values "$a_t$" over a horizontal plane to the expression (17). Moreover, an initial speed value "$v_0$" is calculated by assigning the number of N acceleration values "$a_t$" and the variable K to the expression (28). Furthermore, a position of the center of gravity, "$x_t$" is calculated by assigning the number of N acceleration values "$a_t$" and the initial speed value "$v_0$" to the expression (2). The fluctuation of the center of gravity is a relative position, and thereby an initial position $x_0=0$ is assigned to the expression (2). Accordingly, fluctuation of the center of gravity may be estimated with high accuracy from acceleration values measured by an acceleration sensor even if the subject does not stand still.

Hereinafter, a specific configuration to achieve the above-described processing will be described.

First Embodiment

FIG. 1 is a functional block diagram of a mobile terminal 1 according to the first embodiment. The mobile terminal 1 according to the first embodiment includes an acceleration sensor 101, a measurement result storage unit 103, a correction unit 105, a data storage unit 107, a data read unit 109, a constant storage unit 111, a variable calculation unit 113, a variable storage unit 115, an initial speed calculation unit 117, an initial speed storage unit 119, a center of gravity fluctuation calculation unit 121, a center of gravity fluctuation data storage unit 123, a physical condition database (DB) 125, a physical condition estimation unit 127, a physical condition history data storage unit 129, and an output unit 131. The mobile terminal 1 is assumed to be attached, for example, to clothes of a measurement target subject.

The acceleration sensor 101 measures acceleration at a certain sampling interval and stores the measured acceleration data in the measurement result storage unit 103. The correction unit 105 reads data from the measurement result storage unit 103, conducts a certain correction, and stores the corrected acceleration data in the data storage unit 107. The correction unit 105 includes an offset correction unit 1051, a gravity direction correction unit 1052, a moving direction correction unit 1053, a walking data processing unit 1054, a parameter storage unit 1055, an interval data storage unit 1056, and a template storage unit 1057. Moreover, the data read unit 109 reads corrected acceleration data from the data storage unit 107 at every certain period, and outputs the read data to the variable calculation unit 113, the initial speed calculation unit 117, and the center of gravity fluctuation calculation unit 121. The variable calculation unit 113 calculates a variable "K" according to the above expression (17) by using data from the data read unit 109 and data stored in the constant storage unit 111, and stores the calculated result in the variable storage unit 115. The initial speed calculation unit 117 calculates an initial speed "$v_0$" according to the above expression (28) by using data from the data read unit 109, data stored in the constant storage unit 111 and data stored in the variable storage unit 115 and stores the calculated result in the initial speed storage unit 119. The center of gravity fluctuation calculation unit 121 calculates a position of the center of gravity of a measurement target subject by using data from the data read unit 109, data stored in the constant storage unit 111 and in the initial speed storage unit 119, and stores the calculated result in the center of gravity fluctuation data storage unit 123. The physical condition estimation unit 127 conducts physical condition estimation processing, which will be described later, by using data stored in the center of gravity fluctuation data storage unit 123, the physical condition DB 125, and the physical condition history data storage unit 129. The physical condition estimation unit 127, for example, updates the physical condition history data storage unit 129 based on the processing result, and outputs a physical condition change notification to the output unit 131 if any physical condition is changed. The output unit 131 outputs the changed physical condition based on data stored in the physical condition history data storage unit 129 when the output unit 131 receives the physical condition change notification from the physical condition estimation unit 127.

The processing of the mobile terminal 1 is described by referring to FIGS. 2 to 30. According to the embodiment, a certain correction is applied to acceleration data measured by the acceleration sensor 101 as preprocessing to estimate a fluctuation of the center of gravity. The preprocessing is described by referring to FIGS. 2 to 15.

Figure 2:
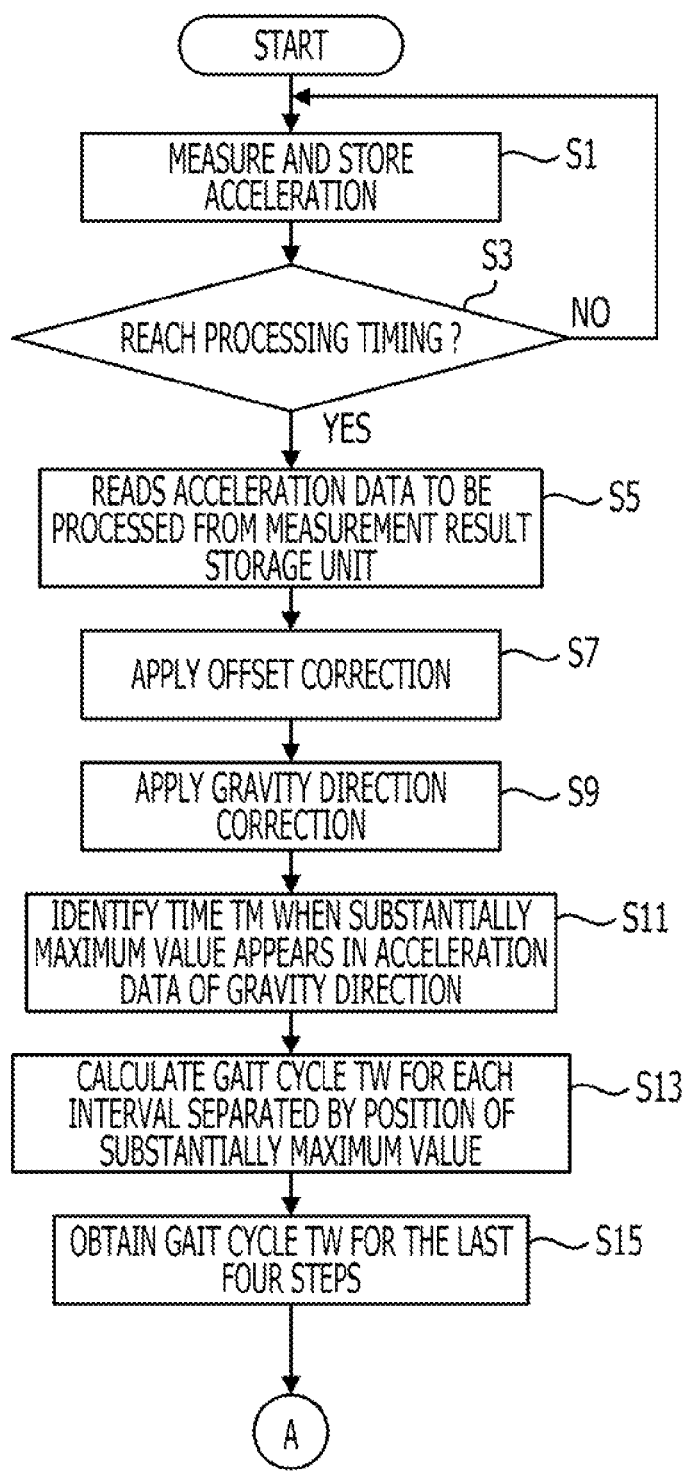
FIG. 2 illustrates a processing flow to apply certain correction processing (preprocessing) to acceleration data.

The acceleration sensor 101 measures acceleration at a certain sampling interval and sequentially stores the measured results in the measurement result storage unit 103 (FIG. 2: Operation S1). The sampling interval is obtained by an inverse number of a sampling frequency (for example, 200 Hz). For example, data illustrated in FIG. 3 is stored in the measurement result storage unit 103. In the example of FIG. 3, the measurement result storage unit 103 stores, time, x-axis acceleration, y-axis acceleration, and z-axis acceleration data.

The correction unit 105 determines whether processing timing is reached (Operation S3). Here, processing is assumed to be conducted at every certain period (for example, 15 seconds). Reaching processing timing is determined by whether a certain period has elapsed since the previous processing. If it is determined that the processing time is not reached (Operation S3: No route), the processing returns to Operation S1.

If the processing timing is determined to be reached (Operation S3: Yes route), the correction unit 105 reads acceleration data to be processed from the measurement result storage unit 103 (Operation S5). In other words, the correction unit 105 reads acceleration data measured for a certain period from the previous processing to the current processing. The offset correction unit 1051 applies an offset correction to the read acceleration data by using data stored in the parameter storage unit 1055 (Operation S7) and stores the corrected acceleration data in a storage device. For example, when an x-axis of an acceleration sensor is a gravity direction, a y-axis is a moving direction, and a z-axis is a right and left direction, if in a stationary state, x-axis acceleration $a_x=1000$ mG, y-axis direction acceleration $a_y=0$ mG, and z-axis acceleration $a_z=0$ mG are supposed to be measured. However, a sensor such as an acceleration sensor have various accuracies. Therefore, measured values that include errors may be calculated such as $a_x=1005$ mG, $a_y=10$ mG, and $a_z=20$ mG in a stationary state. Thus, according to the embodiment, an offset correction is applied so that, for example, a measured value of an acceleration sensor becomes 0 G when acceleration is 0 G, and a measured value of an acceleration sensor becomes 1 G when acceleration is 1 G.

The parameter storage unit 1055 stores data, for example, as illustrated in FIG. 4. In the example of FIG. 4, the parameter storage unit 1055 stores parameter values of XFullScale, XOffset, YFullScale, YOffset, ZFullScale, and ZOffset. For example, acceleration after correction is calculated for x-axis acceleration by ax/XFullScale−Xoffset by using XFullScale and XOffset. For example, FIG. 5 illustrates an example of acceleration data before and after applying an offset correction. FIG. 5 illustrates a case in which XFullScale=1.026 and XOffset=0.015. For example, when an offset correction is applied to an x-axis acceleration at time "10:30:46.002," acceleration after applying the offset correction is $-906/1.026 - 0.015 \approx -883.056$.

The above described parameter values are calculated by conducting the following measurements beforehand. Here, as an example, a method to calculate XFullScale and XOffset are described. For example, the following is the calculation procedure.

1. Align an x-axis with a gravity direction and measure acceleration of the x-axis.
2. Reverse a top and a bottom of the x-axis and measure acceleration of the x-axis.
3. Align a z-axis with a gravity direction and measure acceleration of the x-axis.
4. Reverse a top and a bottom of the z-axis and measure acceleration of the x-axis.

When the value measured at 1 is XFullScale 1 and the value measured at 2 is XFullScale 2, the following calculation is conducted:

XFullScale=(XFullScale 1−XFullScale 2)/2

When the value measured at 3 is XOffset 1 and the values measured at 4 is XOffset 2, the following calculation is performed:

XOffset=(XOffset 1+XOffset 2)/2

The YFullScale may be calculated by aligning the y-axis with the gravity direction and by measuring acceleration of the y-axis (in other words, YFullScale 1 and YFullScale 2). Moreover, the YOffset may be calculated by aligning x-axis with the gravity direction and measuring acceleration of the y-axis (in other words, YOffset 1 and YOffset 2). Moreover, ZFullScale may be calculated by aligning z-axis with the gravity direction at 1 and 2 and measuring acceleration of the z-axis (in other words, ZFullScale 1 and ZFullScale 2). Moreover, ZOffset may be calculated by aligning the y-axis with the gravity direction and measuring acceleration of the z-axis (in other words, ZOffset 1 and ZOffset 2).

Figure 6:
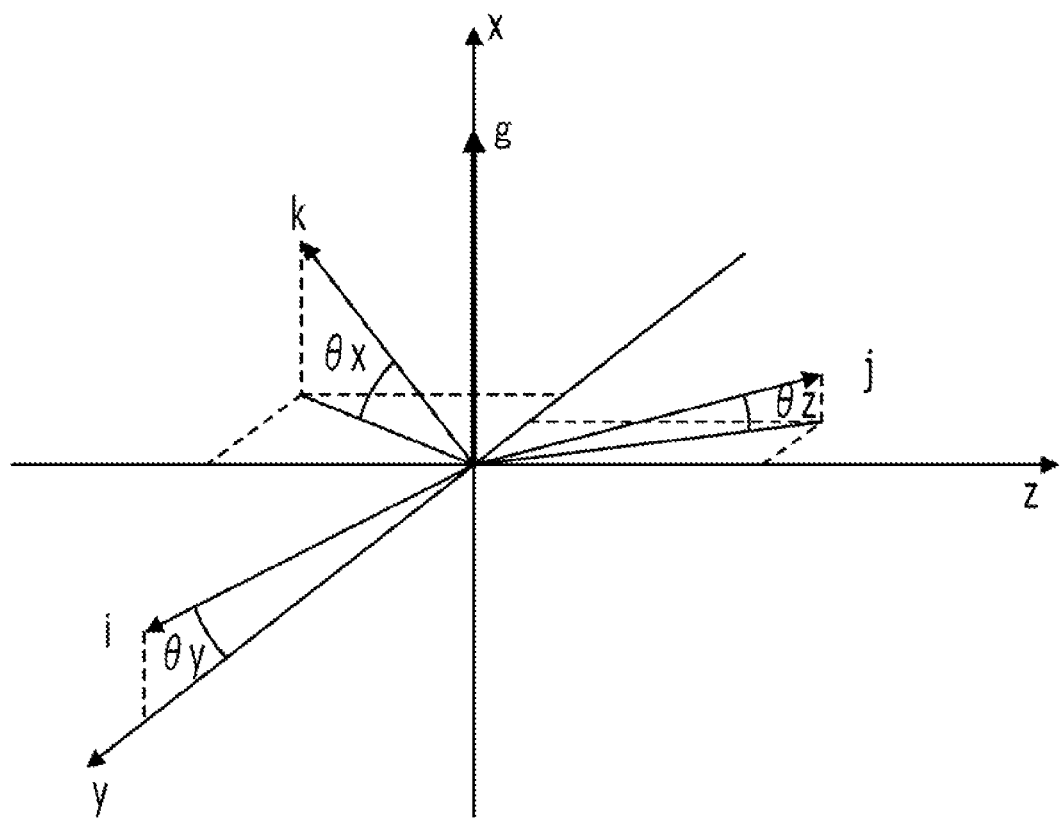
FIG. 6 illustrates angles formed by a unit vector and a y-z plane.

The gravity direction correction unit 1052 applies a gravity direction correction to the acceleration data to which the offset correction is applied (Operation S9) and stores the corrected acceleration data in the storage device. Acceleration data is corrected by converting coordinates using, for example, a frame matrix method. For example, as illustrated in FIG. 6, angles formed by unit vectors, "i", "j", and "k", and a y-z plane are assumed to be "$\theta_y$", "$\theta_z$", and "$\theta_x$" respectively. Here, when components of "i", "j", and "k" directions of gravity acceleration g are "$a_y$", "$a_z$", and "$a_x$" respectively, the "$\theta_y$", "$\theta_z$", and "$\theta_x$" are defined as follows:

$\theta_y = \sin^{-1} a_y/g$ $\theta_z = \sin^{-1} a_z/g$ $\theta_x = \sin^{-1} a_x/g$ A frame matrix $E_0$ is defined as below based on the expressions above.

$$E_0 = \begin{pmatrix} \sin\theta_y & \sin\theta_z & \sin\theta_x \\ \cos\theta_y & -\tan\theta_y \sin\theta_z & -\tan\theta_y \sin\theta_x \\ 0 & \dfrac{\sin\theta_x}{\cos\theta_y} & \dfrac{-\sin\theta_z}{\cos\theta_y} \end{pmatrix}$$

The calculated acceleration "a" may be converted into acceleration in a coordinate system, in which an x-axis is a gravity direction, by "$E_0 * a$" using a matrix $E_0$.

After that, the moving direction correction unit 1053 identifies time TM when a substantially maximum value appears in acceleration data of the gravity direction by using acceleration data obtained after applying a correction to the gravity direction (Operation S11). The moving direction correction unit 1053 calculates a gait cycle Tw of a subject, such as a person, described later, by using the TM identified at Operation S11 for each interval separated by a position of a substantially maximum value, and stores the calculated gait cycle Tw in the interval data storage unit 1056 (Operation S13). For example, the gait cycle is calculated by $Tw = TM_i - TM_{i-1}$. The interval data storage unit 1056 stores data, for example, as illustrated in FIG. 7. In the example of FIG. 7, the interval data storage unit 1056 includes columns of an interval, a start time, an end time, a gait cycle Tw, a walking flag that indicates whether the interval is a walking interval (1: walking interval, 0: stand still interval), and a completion flag that indicates whether standard acceleration subtraction processing, which will be described later, is completed (1. completed, 0: not completed). For example, when $Tw = (TM_2 - TM_1)$ is calculated from $TM_1$ and $TM_7$ for an interval 1, the $TM_1$ is set in the start time column, $TM_2$ is set in the end time column, and $(TM_2 - TM_1)$ is set in the gait cycle Tw column. Moreover, 0 is set in the walking flag and the completion flag.

Figure 8:
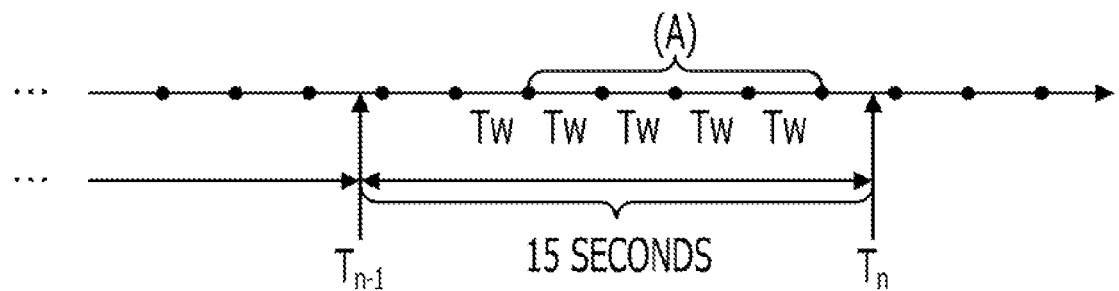
FIG. 8 illustrates processing to obtain a gait cycle for the last four steps.

The moving direction correction unit 1053 obtains a gait cycle Tw for the last four steps of the subject from the interval data storage unit 1056 (Operation S15). For example, as illustrated in FIG. 8, the moving direction correction unit 1053 obtains a gait cycle Tw in a period A that corresponds to the last four steps of the subject at $T_n$. In the example of FIG. 8, time is assumed to be elapsed from the left to the right, and a black circle indicates a position where a substantially maximum value appears. After that the processing transitions to the processing in FIG. 9 through a terminal A.

Figure 9:
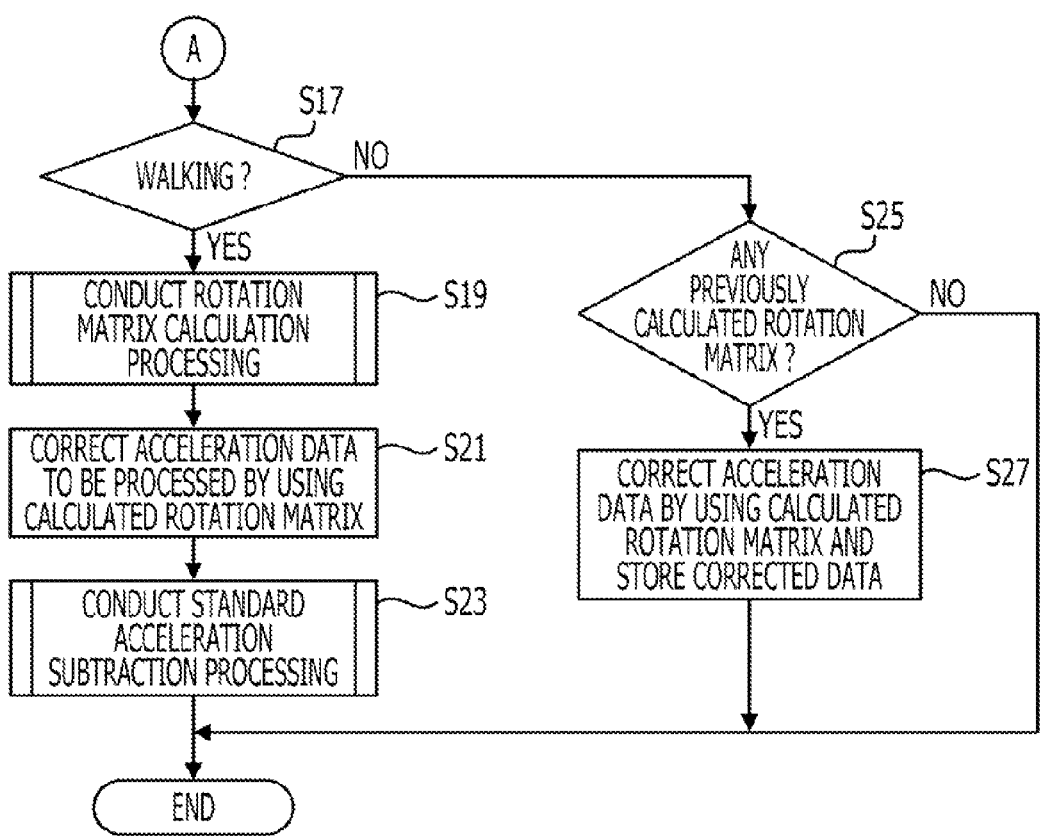
FIG. 9 illustrates a processing flow to apply a certain correction (preprocessing) to acceleration data.

In FIG. 9, after terminal A, the moving direction correction unit 1053 determines whether a subject is walking by using the gait cycle Tw for the last four steps (FIG. 9: Operation S17). For example, the moving direction correction unit 1053 determines that the subject is walking when taking 80-150 [steps/minute] and a variation of the gait cycle for the four steps is within ±10%.

The moving direction correction unit 1053 sets a walking flag for each interval to be processed this time to 1 in the interval data storage unit 1056 when the subject is determined to be walking (Operation S17: Yes route). The moving direction correction unit 1053 conducts rotation matrix calculation processing (Operation S19). The rotation matrix calculation processing will be described by referring to FIG. 10.

Figure 10:
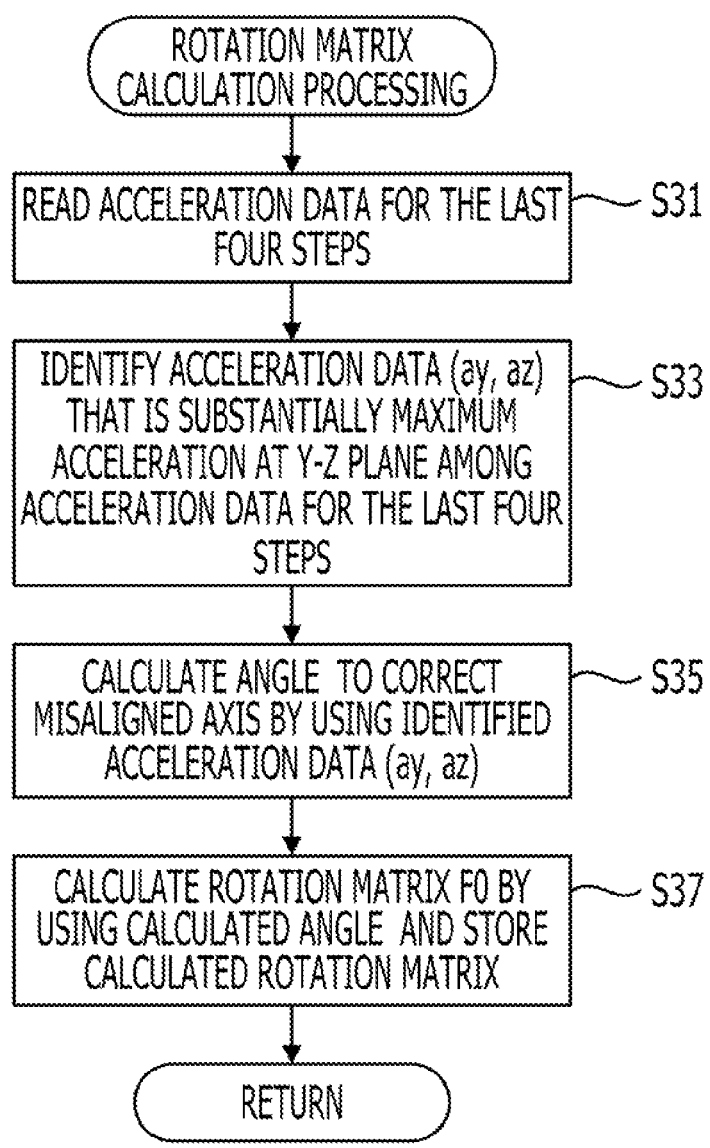
FIG. 10 is a processing flow of rotation matrix calculation processing.

The moving direction correction unit 1053 reads acceleration data for the last four steps of the subject from the storage device in which acceleration data obtained after applying correction to the gravity direction is stored according to data stored in the interval data storage unit 1056 (FIG. 10: Operation S31). The start time and end time for a period corresponding to the last four steps of the subject are obtained from data stored in the interval data storage unit 1056.

The moving direction correction unit 1053 identifies acceleration data $(a_y, a_z)$ that is a substantially maximum acceleration at a y-z plane (Operation S33). For example, when the number of pieces of data in a period for the last four steps is "n", $(a_y, a_z)$ with substantially the largest vector is identified among $(a_{y1}, a_{z1}), (a_{y2}, a_{z2}), (a_{y3}, a_{z3}) \ldots (a_{yn}, a_{zn})$. Substantially, the largest acceleration is caused along the moving direction during walking.

Figure 11:
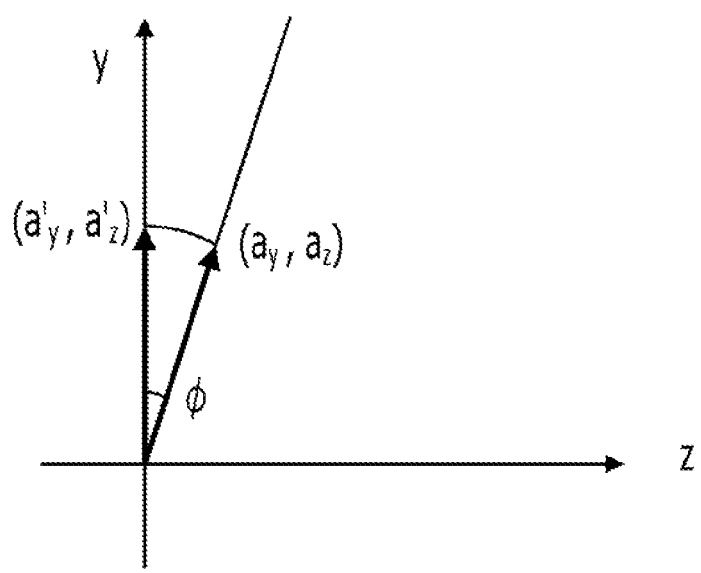
FIG. 11 illustrates an angle $\phi$ formed by a moving direction (y-axis) and vectors (ay, az)
Figure 12:
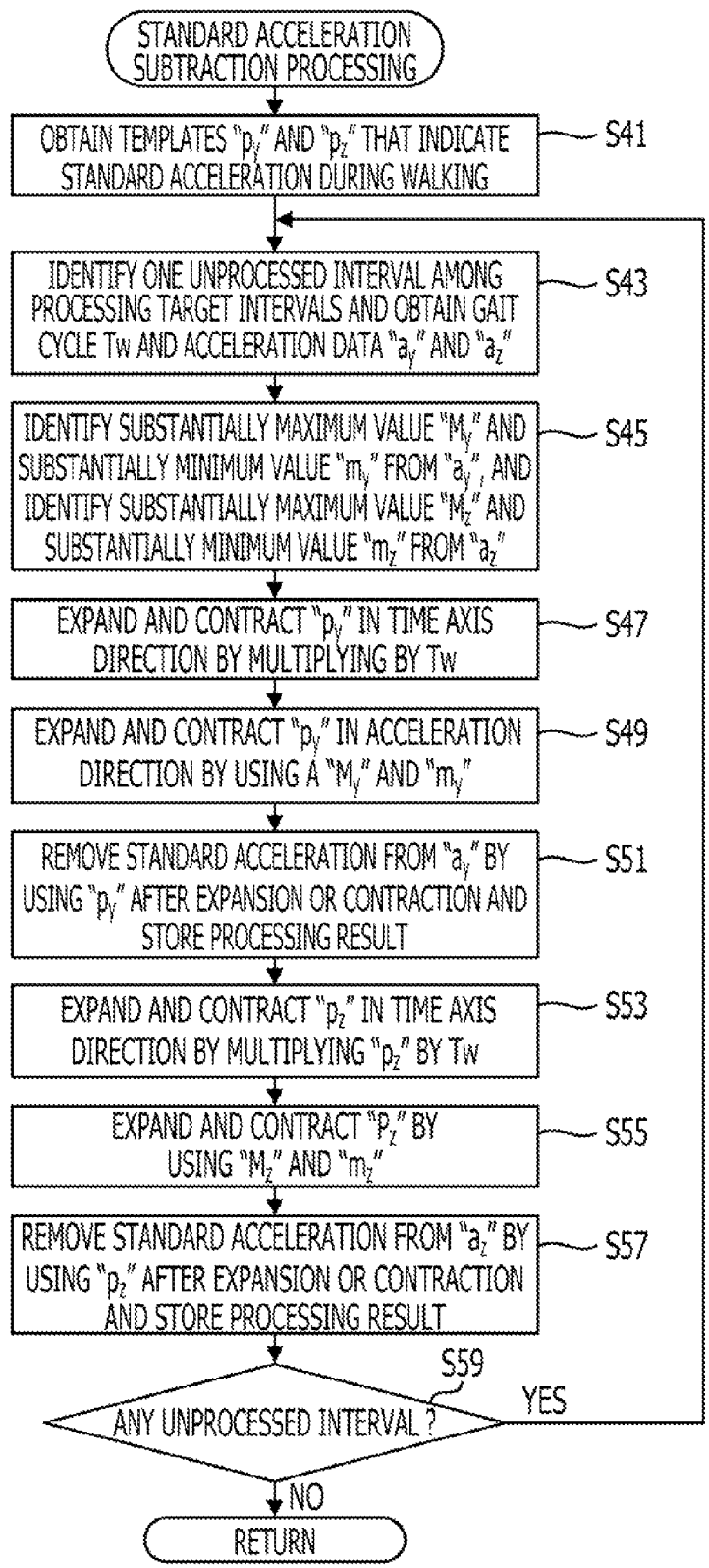
FIG. 12 is a processing flow of subtracting standard acceleration.

The moving direction correction unit 1053 calculates an angle ϕ to correct a misaligned axis of the subject using the identified acceleration data $(a_y, a_z)$ (Operation S35). The angle ϕ is formed by the moving direction (y-axis) and vectors $(a_y, a_z)$ as illustrated in FIG. 11. For example, the angle ϕ is calculated by the following expression.

$$\phi = \tan^{-1}(a_z/a_y)$$

The moving direction correction unit 1053 calculates a rotation matrix $F_0$ by using the calculated angle ϕ and stores the calculated result in the parameter storage unit 1055 (Operation S37). For example, the rotation matrix $F_0$ is calculated by the following expression.

$$F_0 = \begin{pmatrix} \sin\phi & -\cos\phi \\ \cos\phi & \sin\phi \end{pmatrix}$$

After that the processing ends and returns to the original processing.

Returning to the description of FIG. 9, after Operation S19, the moving direction correction unit 1053 corrects acceleration data to be processed using the rotation matrix F0 calculated at Operation S19 (Operation S21), and stores the corrected acceleration data in the storage device. For example, corrected acceleration data is obtained by the following expression when acceleration data before correction is assumed to be a[i] and a[i] $a_y[i]$ and $a_z[i]$, and acceleration data after correction is assumed to be $a'_y[i]$ and $a'_z[i]$.

$$\begin{pmatrix} a'_y[i] \\ a'_z[i] \end{pmatrix} = F_0 \begin{pmatrix} a_y[i] \\ a_z[i] \end{pmatrix}$$

Conversion to align directions of the axes is completed by the processing up to this point.

After that the walking data processing unit 1054 conducts standard acceleration subtraction processing by using data stored in the interval data storage unit 1056 and the template storage unit 1057 (Operation S23). The standard acceleration subtraction processing will be described by referring to FIG. 12.

The walking data processing unit 1054 obtains a template "$p_y$" that indicates a standard acceleration of a subject of a moving direction during walking and a template "$p_z$" that indicates standard acceleration of a right and left direction of a subject during walking from the template storage unit 1057 (Operation S41).

Figure 13:
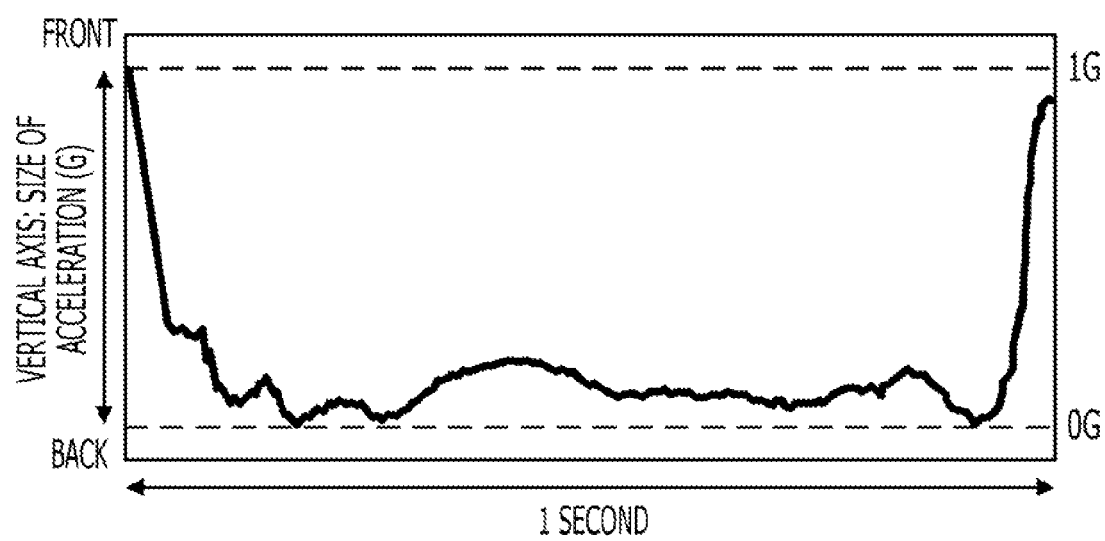
FIG. 13 illustrates an example of a template indicating standard acceleration during walking.

FIG. 13 illustrates an example of templates stored in the template storage unit 1057. FIG. 13 illustrates an example of a template that indicates standard acceleration of a moving direction of a subject during walking. In FIG. 13, the horizontal axis indicates a gait cycle, while the vertical axis indicates acceleration. A template is, for example, data generated from characteristic patterns of acceleration during walking. The gait cycle is normalized so as to be, for example, 60 (steps/minute). The acceleration is assumed to be normalized so that a substantially maximum value is 1 G and a substantially minimum value is 0 G, for example.

As described in a non-patent document 1 (Ogura, Ohbuchi, Kojima, Furuna, and Shiomi, "Identifying the Characteristic Acceleration Patterns by Using Accelerographic Analysis of the Pelvis in Normal Working—review on identifying a common characteristic pattern from acceleration data of young people," Rigakuryoho Kagaku, VOL. 20; No. 2; PAGE. 171-177 (2005)), characteristic patterns of acceleration of a first step of a left foot and that of a right foot differ in standard acceleration of a right and left direction. Thus, according to the embodiment, two types of templates are prepared. One is a template that indicates standard acceleration of a subject for the first step of the left foot and the other is that for the right foot.

The walking data processing unit 1054 identifies one unprocessed interval among walking intervals according to data stored in the interval data storage unit 1056. For example, one interval is identified from intervals in which the walking flag is 1 and the completion flag is 0. The walking data processing unit 1054 obtains a gait cycle Tw that corresponds to the identified interval from the interval data storage unit 1056 and obtains acceleration data "$a_y$" and "$a_z$" from the storage device (Operation S43). Here, acceleration data of the moving direction is indicated as "$a_y$", while that of the right and left direction is indicated as "$a_z$." The walking data processing unit 1054 identifies a substantially maximum value "My" and a substantially minimum value "$m_y$" from the obtained acceleration data "$a_y$." Likewise, the walking data processing unit 1054 identifies a substantially maximum value "$M_z$" and a substantially minimum value "$m_z$" from the obtained acceleration data "$a_z$" (Operation S45).

Figure 14:
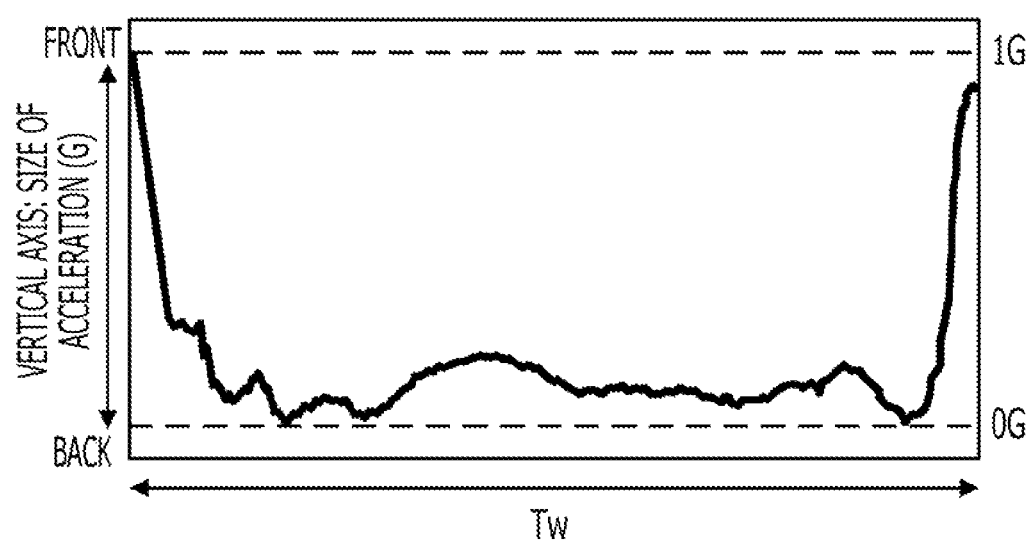
FIG. 14 illustrates a case when the template of FIG. 13 is contracted in a time-axis direction.

The walking data processing unit 1054 expands and contracts the template "py" in the time axis direction by multiplying by Tw (Operation S47). For example, when the template illustrated in FIG. 13 is contracted along the time axis direction by multiplying the template by Tw, the template is transformed as illustrated in FIG. 14. FIG. 14 illustrates an example when the template illustrated in FIG. 13 is contracted in the time axis direction (horizontal axis). Interpolation is applied when the template is expanded to the time axis direction.

The walking data processing unit 1054 expands and contracts the template "$p_y$", which is expanded or contracted along the time axis direction, in acceleration direction by using a substantially maximum value "$M_y$" and a substantially minimum value "$m_y$" (Operation S49). As described above, the template is normalized so that a substantially maximum value is 1 G and a substantially minimum value is 0 G. Accordingly, the template is transformed so as to correspond to amplitude of the measured acceleration. For example, the template is transformed by using the expression below.

$$(M_y-m_y)*p_y+m_y$$

Figure 15:
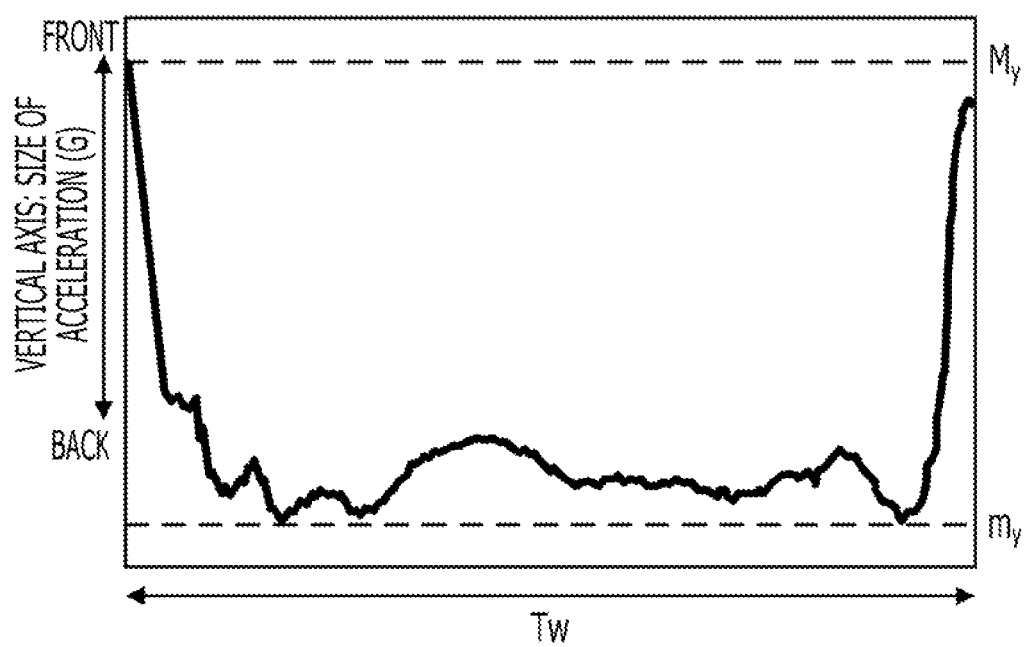
FIG. 15 illustrates a case when the template of FIG. 14 is expanded in an acceleration direction.

For example, when the template in FIG. 14 is expanded to the acceleration direction, the template is transformed as illustrated in FIG. 15. FIG. 15 illustrates an example when the template in FIG. 14 is expanded in the acceleration direction (vertical axis).

The walking data processing unit 1054 removes standard acceleration from "ay" in the identified interval by using the template "$p_y$" after expansion or contraction and stores the processing result in the data storage unit 107 (Operation S51). For example, when standard acceleration obtained from the expanded or contracted template "$p_y$" is assumed to be "$a_{py}$," acceleration after removing the standard acceleration is calculated by the following expression:

$$a_y-a_{py}$$

The walking data processing unit 1054 determines whether the identified interval is the interval of the first step of the left foot or that of the right foot of a subject from "$a_z$" in the identified interval. In the above-described processing, a rotation matrix $F_0$ is applied so that the moving direction becomes a positive direction. Thus, for example, in the case of the right side coordinate system, applying the rotation matrix $F_0$ makes the left direction the positive direction. In this case, an average value of "$a_z$" in the identified interval is calculated and if the average value is a positive value, the interval is determined to be the first step of the right foot, and if the average value is a negative value, the interval is determined to be the first step of the left foot. In the processing below, an applicable template either the template that indicates standard acceleration for the first step of the left foot or that indicates standard acceleration for the first step of the right foot is used.

The walking data processing unit 1054 expands and contracts the template "$p_z$" in the time axis direction by multiplying the template "$p_z$" by Tw (Operation S53). The walking data processing unit 1054 expands and contracts the template "$p_z$", which is expanded or contracted along the time axis direction, along the acceleration axis direction by using a substantially maximum value "$M_z$" and a substantially minimum value "$m_z$" (Operation S55). For example, the template is transformed by using the following expression.

$$(M_z-m_z)*p_z+m_z$$

The walking data processing unit 1054 removes standard acceleration from "$a_z$" in the identified interval by using the template "$p_z$" after expansion or contraction and stores the processing result in the data storage unit 107 (Operation S57). For example, when standard acceleration obtained from the expanded or contracted template "$p_z$" is assumed to be "$a_{pz}$" acceleration after removing the standard acceleration is calculated by the following expression:

$$a_z-a_{pz}$$

The walking data processing unit 1054 sets a completion flag of the identified interval in the interval data storage unit 1056 to 1 (completed).

The walking data processing unit 1054 determines whether there is any unprocessed interval among walking intervals (Operation S59). When there is any unprocessed interval among walking intervals (Operation S59: Yes route), the processing returns to Operation S43, and repeats the above described processing. Meanwhile, when there is no unprocessed interval among walking intervals (Operation S59: No route), the processing ends and returns to the original processing (FIG. 9). Standard acceleration during walking may be removed from the measured acceleration by conducting the above-described processing.

Now returning to the description of FIG. 9, the processing ends after Operation S23.

When the subject is determined not to be walking at Operation S17 in FIG. 9 (Operation S17: No route), the processing transitions to Operation S25. The moving direction correction unit 1053 determines whether there is any rotation matrix $F_0$ that is previously calculated (Operation S25). As described above, the rotation matrix $F_0$ calculated by the rotation matrix calculation processing is stored in the parameter storage unit 1055, thus, determination at Operation S25 is made by whether the rotation matrix $F_0$ is stored in the parameter storage unit 1055. When there is any previously calculated rotation matrix $F_0$ (Operation S25: Yes route), the moving direction correction unit 1053 corrects a processing target acceleration data by using the previously calculated rotation matrix $F_0$ (Operation S21) and stores the corrected acceleration data in the data storage unit 107 (Operation S27). The correction processing is substantially the same as the processing at described for Operation S21, and therefore will not be repeated here. After that the processing ends.

When there is no previously calculated rotation matrix $F_0$ (Operation S25: No route), processing ends without conducting Operation S27.

Conducting the above-described processing allows acceleration data obtained by the acceleration sensor to be corrected. The corrected acceleration data is stored in the data storage unit 107. Moreover, noise may be removed, for example, by applying a low-pass filter to the obtained acceleration data.

Figure 16:
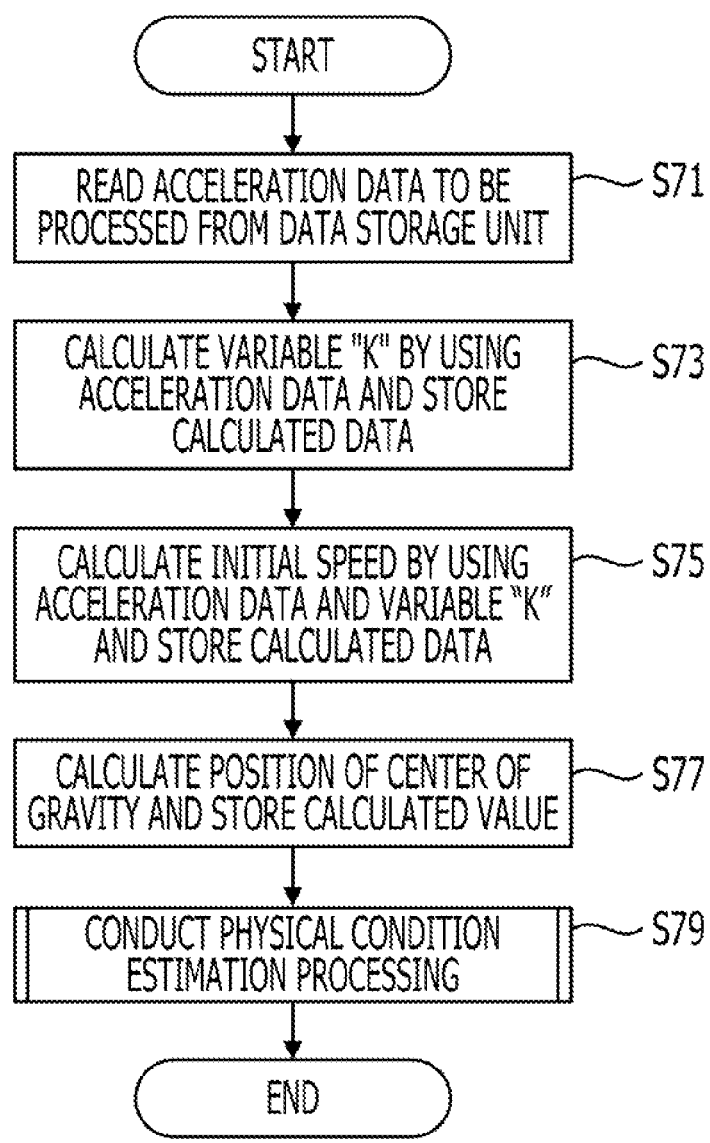
FIG. 16 illustrates a processing flow to estimate fluctuation of the center of gravity and a physical condition.
Figure 17:
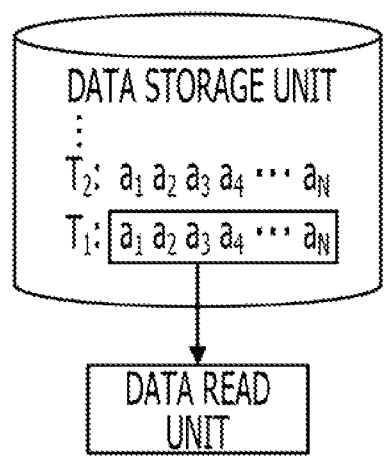
FIG. 17 schematically illustrates processing to read data from the data storage unit.

Processing to estimate a fluctuation of the center of gravity and physical condition of a subject will be described by referring to FIGS. 16 to 30. According to the embodiment, a processing flow as illustrated in FIG. 16 is conducted at every certain period (for example, at every 15 seconds). When processing timing is reached, the data read unit 109 reads acceleration data to be processed from the data storage unit 107 (Operation S71 in FIG. 16), and outputs the read acceleration data to the variable calculation unit 113, the initial speed calculation unit 117, and the center of gravity fluctuation calculation unit 121. As schematically illustrated in FIG. 17, when the number of samplings in a certain period is N, the data read unit 109 reads the number of N corrected acceleration values "$a_i$" from the data storage unit 107.

The variable calculation unit 113 assigns the number of N acceleration values "$a_i$" from the data read unit 109 and a certain constant stored in the constant storage unit 111 to the above expression (17), calculates a variable "K" and stores the calculated result in the variable storage unit 115 (Operation S73). At Operation S73, a variable "K" for a moving direction is calculated by using the number of N acceleration values "$a_i$" of the moving direction and a variable "K" for a right and left direction is calculated by using the number of N acceleration "$a_i$" of the right and left direction. Here, the processing will be described by assuming the y-axis is the moving direction while the z-axis is the right and left direction. The constant storage unit 111 stores data that indicates, for example, a sampling interval $\Delta t$, the number of samplings N, and a certain period. The variable storage unit 115 stores data, for example, as illustrated in FIG. 18. In the example of FIG. 18, the variable storage unit 115 includes columns of a period, a value of K (a moving direction), and a value of K (a right and left direction).

The initial speed calculation unit 117 assigns the number of N acceleration values from the data read unit 109, a variable K stored in the variable storage unit 115 and a certain constant stored in the constant storage unit 111 to the above expression (28), calculates an initial speed $v_0$, and stores the calculated result in the initial speed storage unit 119 (Operation S75). At Operation S75, an initial speed value "$v_0$" for the moving direction is calculated by using the number of N acceleration "$a_i$" and the variable "k" for the moving direction. Likewise, an initial speed value "$v_0$" for the right and left direction is calculated by using the number of N acceleration "$a_i$" and the variable "k" for the right and left direction. The initial speed storage unit 119 stores data, for example, as illustrated in FIG. 19. In the example of FIG. 19, the initial speed storage unit 119 includes columns of a period, an initial speed (a moving direction) and an initial speed (right and left direction).

The center of gravity fluctuation calculation unit 121 assigns the number of N acceleration values from the data read unit 109, an initial speed value $v_0$ stored in the initial speed storage unit 119 and a certain constant stored in the constant storage unit 111 to the above expression (2) and calculates a position of the center of gravity of the subject and stores the calculated result in the center of gravity fluctuation data storage unit 123 (Operation S77). At Operation S77, a coordinate value of a Y-axis is calculated by using the number of N acceleration values "$a_i$" and an initial speed value $v_0$ for a moving direction. Similarly, a coordinate value of an X-axis is calculated by using the number of N acceleration values "$a_i$" and an initial speed value $v_0$ for the right and left direction. The center of gravity fluctuation data storage unit 123 stores data, for example, as illustrated in FIG. 20. In the example of FIG. 20, the center of gravity fluctuation data storage unit 123 includes columns of a position (Y-axis) and a position (Z-axis).

Figure 21:
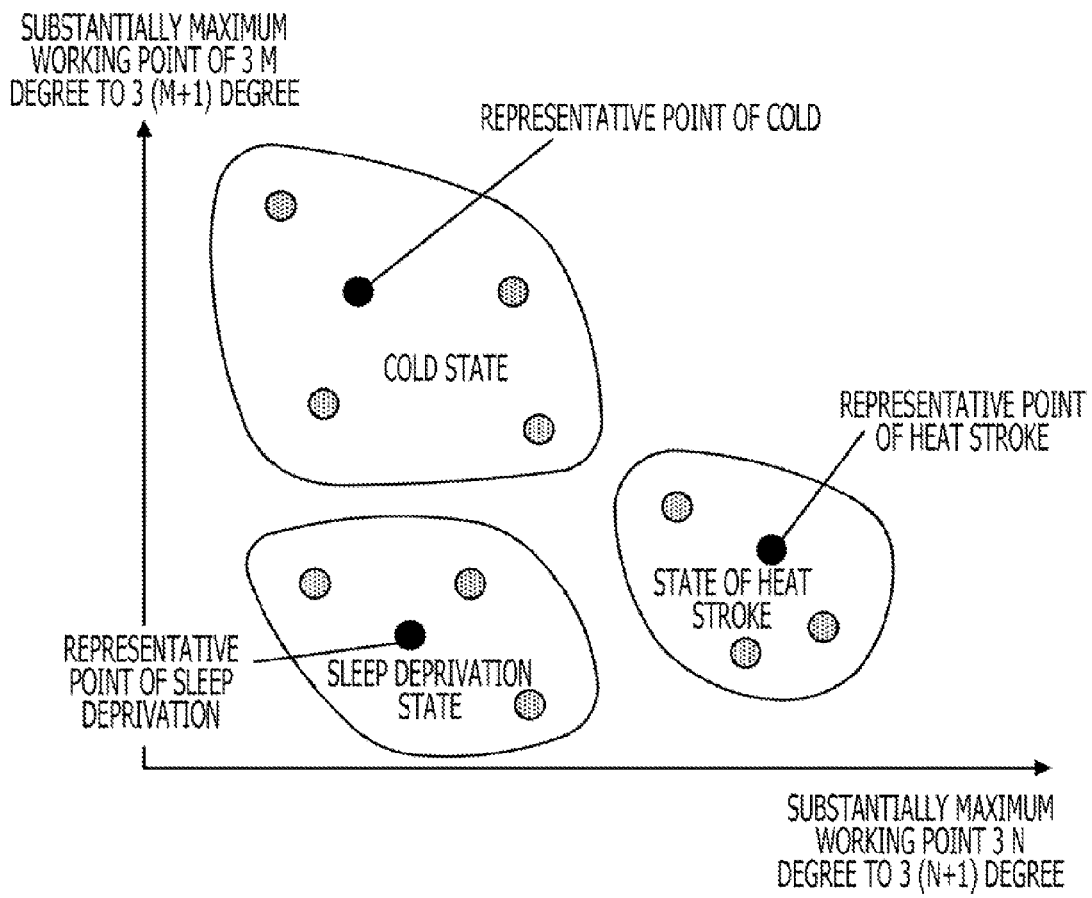
FIG. 21 schematically illustrates representative data used for a cluster analysis.

After that, the physical condition estimation unit 127 conducts physical condition estimation processing of the subject by using data stored in the center of gravity fluctuation data storage unit 123, the physical condition DB 125, and the physical condition history data storage unit 129 (Operation S79) and ends the processing. In the physical condition estimation processing, representative data for a plurality of physical condition candidates (for example, fatigue, sleep deprivation, cold, heat stroke, intoxication, and nervousness) is prepared and a physical condition is estimated for a subject by conducting a cluster analysis. For example, FIG. 21 schematically illustrates representative data used for the cluster analysis. FIG. 21 illustrates representative data of a cold state, sleep deprivation, and heat stroke. Hereinafter, the physical condition estimation processing will be described by referring to FIG. 22.

Figure 22:
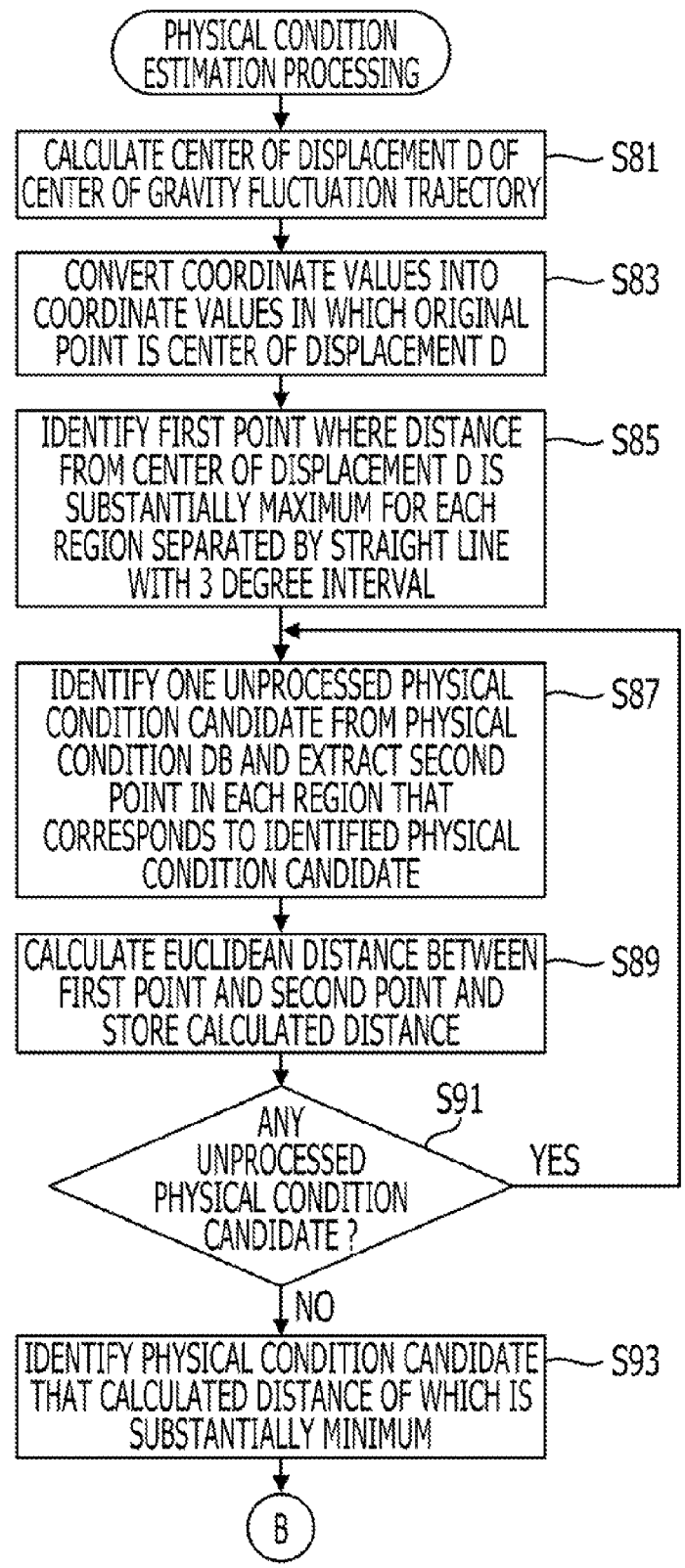
FIG. 22 illustrates a processing flow to estimate a physical condition.
Figure 24:
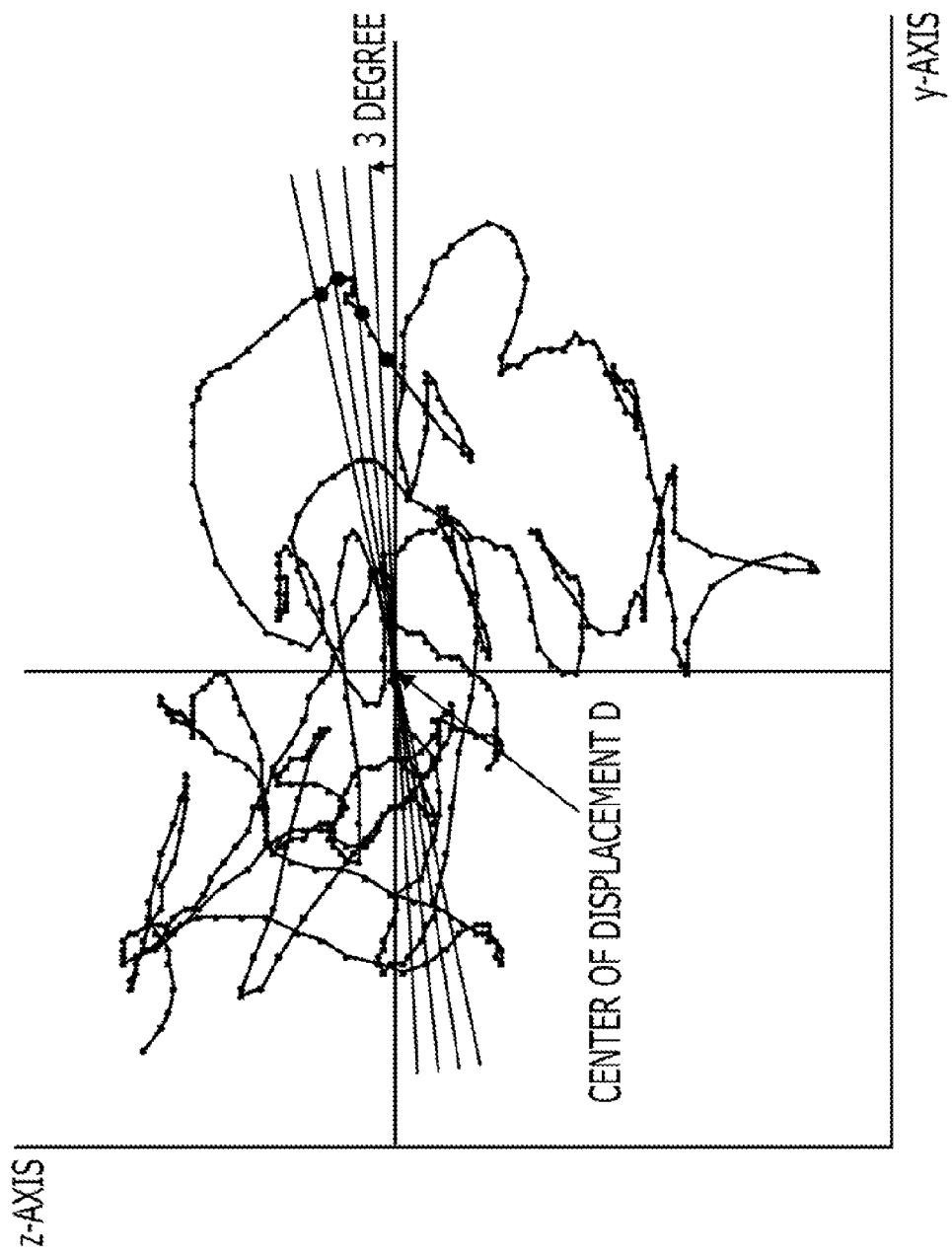
FIG. 24 schematically illustrates processing to identify a first point.

The physical condition estimation unit 127 reads position data from the center of gravity fluctuation data storage unit 123 and calculates a center of displacement D of center of gravity fluctuation trajectory (FIG. 22: Operation S81). At Operation S81, an average value of coordinate values of y-axis and z-axis are obtained as the center of displacement D. The physical condition estimation unit 127 converts coordinate values stored in the center of gravity fluctuation data storage unit 123 into coordinate values in which an original point is the center of displacement D and stores the converted value in the storage device (Operation S83). For example, converting data illustrated in FIG. 20 into a relative position in which an original point is the center of displacement D results in data as illustrated in FIG. 23. The physical condition estimation unit 127 identifies a point where a distance from the center of displacement D is substantially the maximum among points indicated by coordinate values stored in the center of gravity fluctuation data storage unit 123 for each region separated by a straight line that passes through the center of displacement D with a 3 degree interval (Operation S85). FIG. 24 schematically illustrates the processing of Operation S85. As illustrated in FIG. 24, a yz plane is divided into regions with a 3 degree interval by straight lines that pass through the center of displacement D. A point where a distance from the center of displacement D is substantially the maximum (hereinafter, the first point) is identified for each region. For example, as illustrated in FIG. 25, a region range, a region number, and a distance from the center of displacement D to the first point are stored in the storage device for each region.

The physical condition estimation unit 127 identifies one unprocessed physical condition candidate from the physical condition DB 125 and extracts a representative point in each region that corresponds to the physical condition candidate (hereinafter, referred to as the second point) (Operation S87). The physical condition DB 125 stores data, for example, as illustrated in FIG. 26. In the example of FIG. 26, the physical condition DB 125 includes columns of a region range, a region number, a normal condition, a fatigue condition and so on. The physical condition DB 125 stores data at representative points in each region that corresponds to each physical condition candidate. The position of a representative point is indicated, for example, by the coordinate values and vector values.

The physical condition estimation unit 127 calculates an Euclidean distance between the first point and the second point and stores the calculated value in the storage device (Operation S89). According to the embodiment, it is assumed that data in the first point (a distance from coordinate values or a distance from the center of displacement D to the first point) is "ri" ("i" is a variable that indicates a region number), and a data value at a representative point for k th physical condition candidate (coordinate values or a vector value) is "Rki" and the Euclidean distance is calculated by the expression below:

$$\sqrt{\sum_{i=0}^{119}(r_i - Rk_i)^2}$$

The physical condition estimation unit 127 determines whether there is any unprocessed physical condition candidate in the physical condition DB 125 (Operation S91). When there is any unprocessed physical condition candidate (Operation S91: Yes route), the processing returns to Operation S87 and the above-described processing is repeated.

When there is no unprocessed physical condition candidate (Operation S91: No route), the physical condition estimation unit 127 identifies a physical condition candidate the calculated distance of which is substantially the minimum based on data stored in the storage device (Operation S93). After that the processing returns to the processing illustrated in FIG. 27 through the terminal B.

Figure 27:
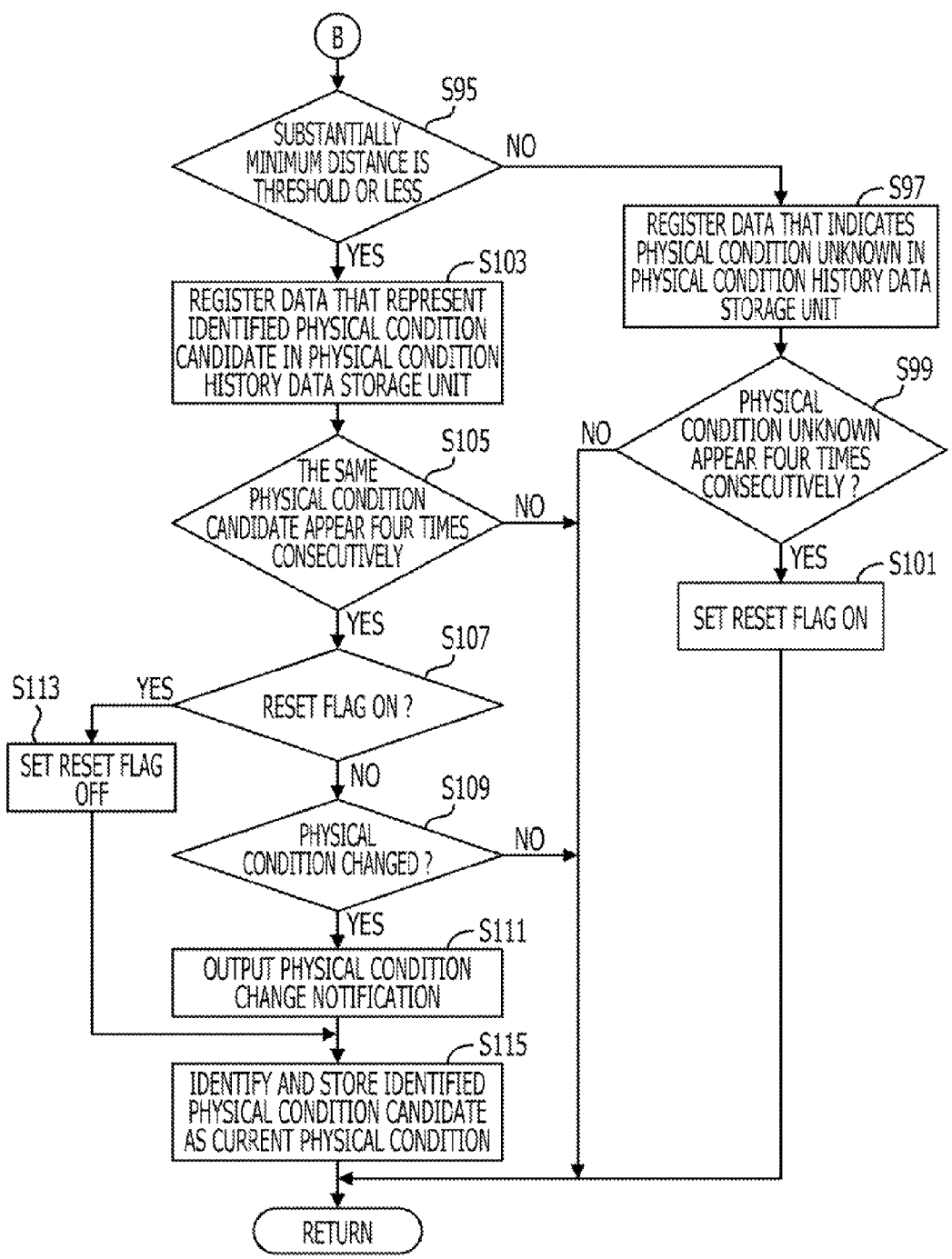
FIG. 27 illustrates a processing flow to estimate a physical condition.
Figure 30:
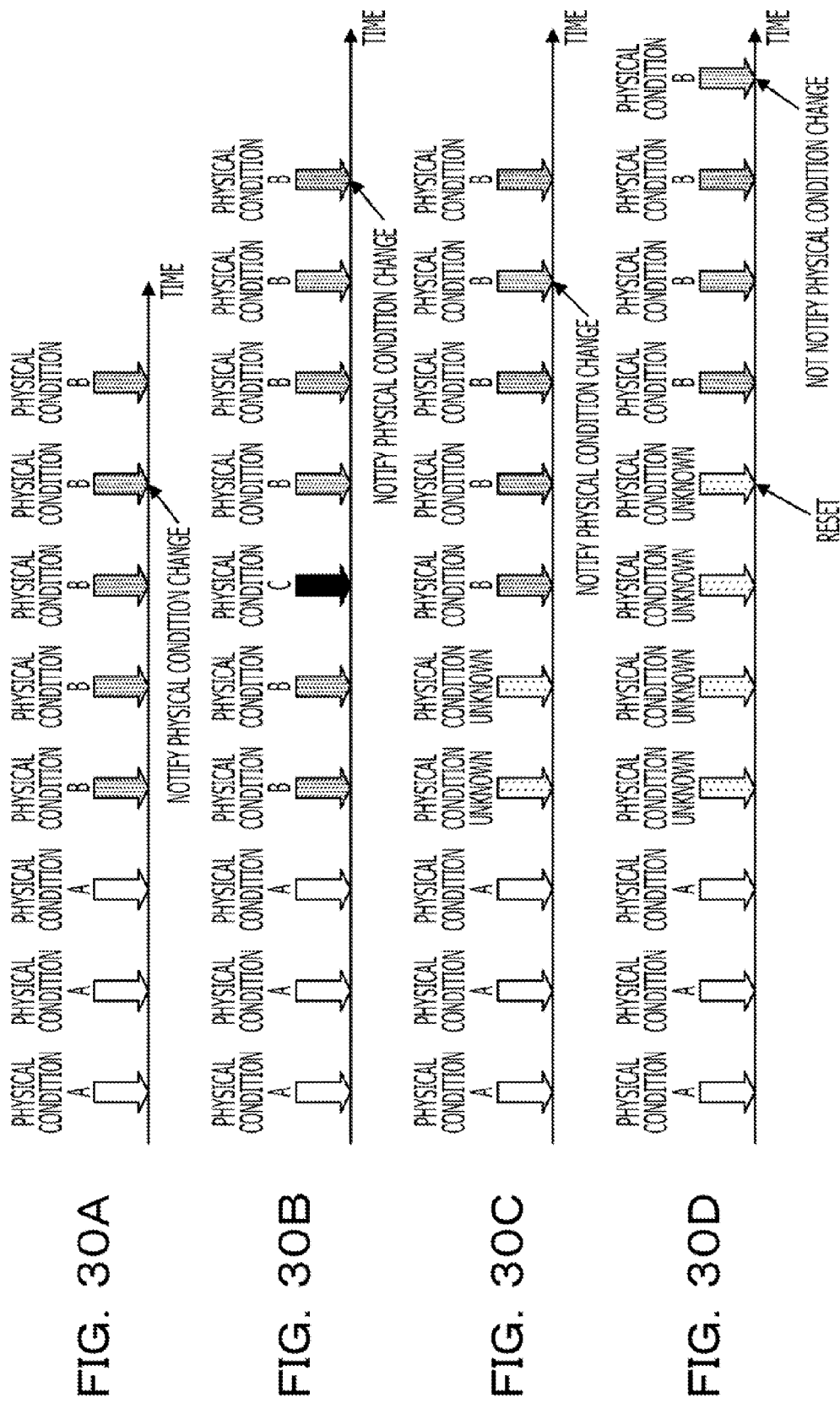
FIGS. 30A to 30D illustrate examples of changes in physical conditions.

In FIG. 27, after terminal B, the physical condition estimation unit 127 determines whether a substantially minimum distance among the calculated distances is equal to or less than a certain threshold (FIG. 27: Operation S95). When the substantially minimum distance is not equal to or not less than the certain threshold (Operation S95: No route), in other words, when the substantially minimum distance is larger than the certain threshold, the physical condition estimation unit 127 determines the physical condition unknown. The physical condition estimation unit 127 registers data that indicates the physical condition unknown in the physical condition history data storage unit 129 (Operation S97). The physical condition history data storage unit 129 stores data as illustrated in FIGS. 28 and 29. FIG. 28 illustrates an example of physical condition history data stored in the physical condition history data storage unit 129. FIG. 29 illustrates an example of physical condition management data stored in the physical condition history data storage unit 129. At operation S97, a record including data that indicates physical condition unknown is added to the bottom of the physical condition history data (FIG. 28).

The physical condition estimation unit 127 determines whether the physical condition unknown appears four times consecutively according to the physical condition history data (Operation S99). When the physical condition unknown appears four times consecutively (Operation S99: Yes route), the physical condition estimation unit 127 sets a reset flag included in the physical condition management data to ON (Operation S101). Then, the processing ends and returns to the original processing. When the physical condition unknown does not appear four times consecutively (Operation S99: No route), the processing ends and returns to the original processing.

Meanwhile, when the substantially minimum distance is determined to be equal to or less than the threshold at Operation S95 (Operation S95: Yes route), the physical condition estimation unit 127 registers data that represents the identified physical condition candidate in the physical condition history data storage unit 129 (Operation S103). For example, a record including data that represents the identified physical condition candidate is added to the bottom of the physical condition history data. The physical condition estimation unit 127 determines whether the same physical condition candidate appears four times consecutively (Operation S105). When the same physical condition candidate does not appear four times consecutively (Operation S105: No route), the processing ends without conducting the processing described below and returns to the original processing.

When the same physical condition candidate appears four times consecutively (Operation S105: Yes route), the physical condition estimation unit 127 determines whether a reset flag included in the physical condition management data is set to ON (Operation S107). When the reset flag is set to OFF (Operation S107: No route), the physical condition estimation unit 127 determines whether the physical condition is changed (Operation S109). For example, the physical condition candidate that appears four times consecutively and the current physical condition included in the physical condition management data are compared. When the compared two match, it is determined that there is no change, whereas when the two do not match, it is determined that the physical condition of the subject is changed. When the physical condition is not changed (Operation S109: No route), the processing ends without conducting the processing described below and returns to the original processing.

Meanwhile, when the physical condition of the subject is determined to be changed (Operation S109: Yes route), the physical condition estimation unit 127 instructs the output unit 131 to output a physical condition change notification. The output unit 131 outputs a physical condition change notification including data representing the changed physical condition according to physical condition history data stored in the physical condition history data storage unit 129 in response to the instruction from the physical condition estimation unit 127 (Operation S111). For example, a changed physical condition is displayed when the mobile terminal device 1 includes a display device, or audio data is output when the terminal device 1 includes, for example, a speaker. After that the processing transitions to Operation S115.

When a reset flag is set to ON (Operation S107: Yes route), the physical condition estimation unit 127 sets the reset flag to OFF (Operation S109). After that the processing transitions to Operation S115.

After Operations S111 or S113, the physical condition estimation unit 127 identifies the identified physical condition candidate as a current physical condition of the subject and stores the identified physical condition in the physical condition history data storage unit 129 (Operation S115). For example, data representing the identified physical condition candidate is set to the physical condition management data in the physical condition history data storage unit 129. After that the processing ends and returns to Operation S81.

Specific examples will be described by referring to FIGS. 30A to 30D in order to facilitate a better understanding of the physical condition estimation processing. For example, FIG. 30A illustrates the first example of a change in physical conditions. In FIG. 30A, the physical condition B is consecutively detected after the physical condition A. As illustrated in FIG. 30A, after physical condition B is consecutively detected four times, it is determined that the physical condition is changed to the physical condition B and the physical condition change is notified.

FIG. 30B illustrates the second example of a physical condition change. In FIG. 30B, the physical conditions are detected in order of the physical condition A, the physical condition B for two times, and the physical condition C for one time. As illustrated in FIG. 30B, after physical condition B is consecutively detected four times, it is determined that the physical condition of the subject is changed to the physical condition B and the physical condition change is notified.

Furthermore, FIG. 30C illustrates the third example of a physical condition change of a subject. In FIG. 30C, the physical conditions are detected in order of the physical condition A, the physical condition unknown for two times, and the physical condition B consecutively. As illustrated in FIG. 30C, after the physical condition unknown is detected and physical condition B is consecutively detected four times, it is determined that the physical condition of the subject is changed to the physical condition B and the physical condition change is notified.

FIG. 30D illustrates the fourth example of a physical condition change. In FIG. 30D, the physical conditions are detected in order of the physical condition A, then the physical condition unknown for four times consecutively, and the physical condition B consecutively. In this case, the reset flag is set to ON when the physical condition unknown is consecutively detected for four times. Thus, the physical condition change is not notified even if the physical condition B is consecutively detected for four times.

A position of the center of gravity of a subject may be calculated with high accuracy based on acceleration measured by the acceleration sensor 101 even when a subject is not standing still at the start of measurement by conducting the above-described processing. Furthermore, fluctuation of the center of gravity of a subject may be estimated from the calculated center of gravity with high accuracy, and thereby the physical condition may be estimated.

Second Embodiment

Figure 31:
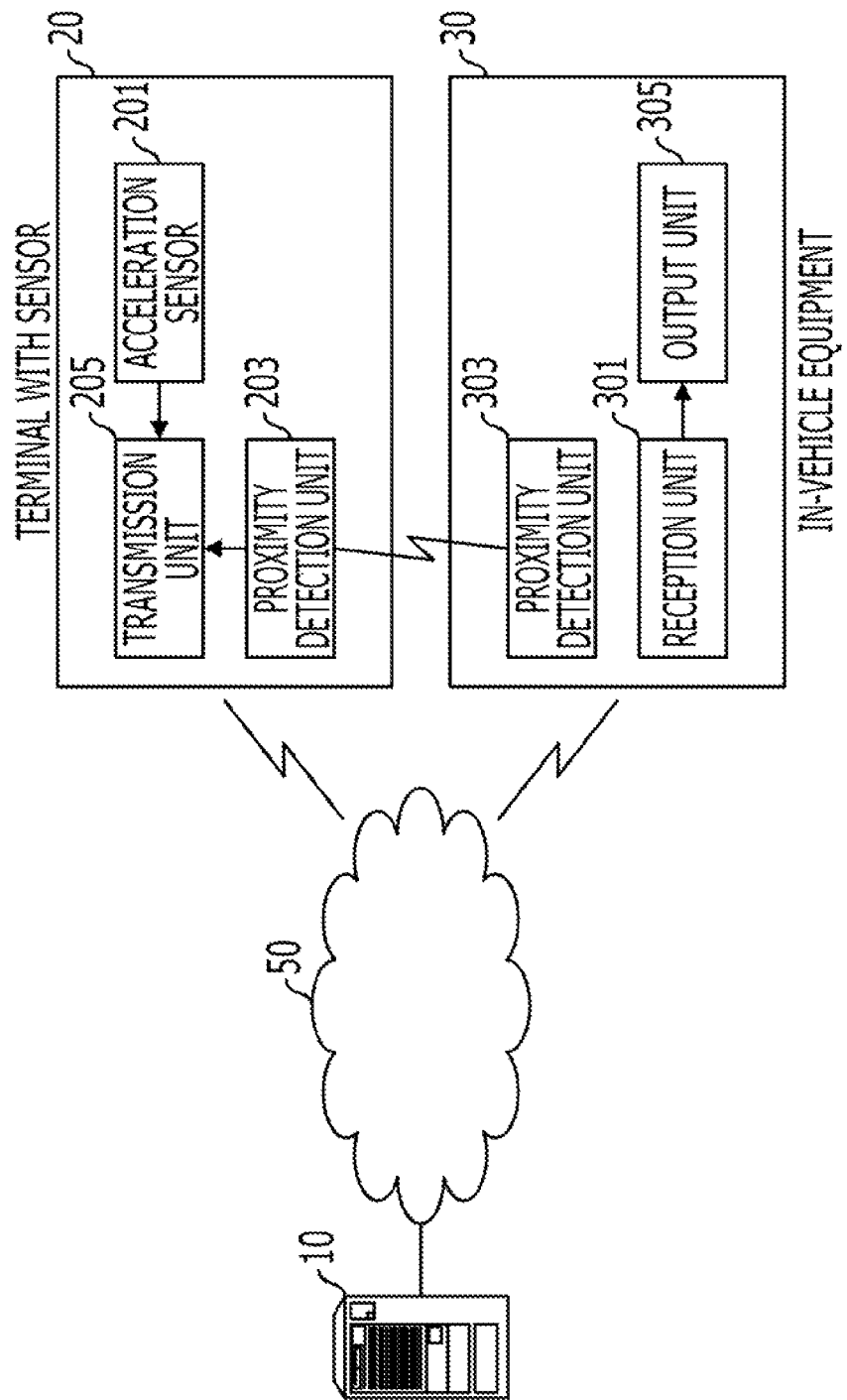
FIG. 31 illustrates a configuration of a system according to a second embodiment.

According to the first embodiment, a standalone type system is described; however the embodiment may be modified to a client-server type system. FIG. 31 illustrates a configuration of a system when a client-server system is achieved. As illustrated in FIG. 31, for example, a server 10, a terminal 20 with a sensor, and an in-vehicle equipment 30 are wired or wirelessly coupled to a network 50, for example, the Internet. The terminal 20 with a sensor is attached, for example, to clothes of a user.

The terminal 20 with a sensor includes an acceleration sensor 201, a proximity detection unit 203, and a transmission unit 205. The acceleration sensor 201 measures acceleration of the user at a certain sampling interval and sequentially outputs the measured acceleration to the transmission unit 205. The transmission unit 205 sequentially transmits acceleration measured by the acceleration sensor 201 to the server 10 through the network 50. The proximity detection unit 203 transmits identification information of the terminal 20 with a sensor and the in-vehicle equipment 30 (for example, an IP address) to the transmission unit 205 when the proximity detection unit 203 detects the in-vehicle equipment 30 approaching. The transmission unit 205 transmits a physical condition information transmission request that includes the identification information of the in-vehicle equipment 30 to the server 10 through the network 50 when the transmission unit 205 receives the identification information of the in-vehicle equipment 30 from the proximity detection unit 203.

Figure 32:
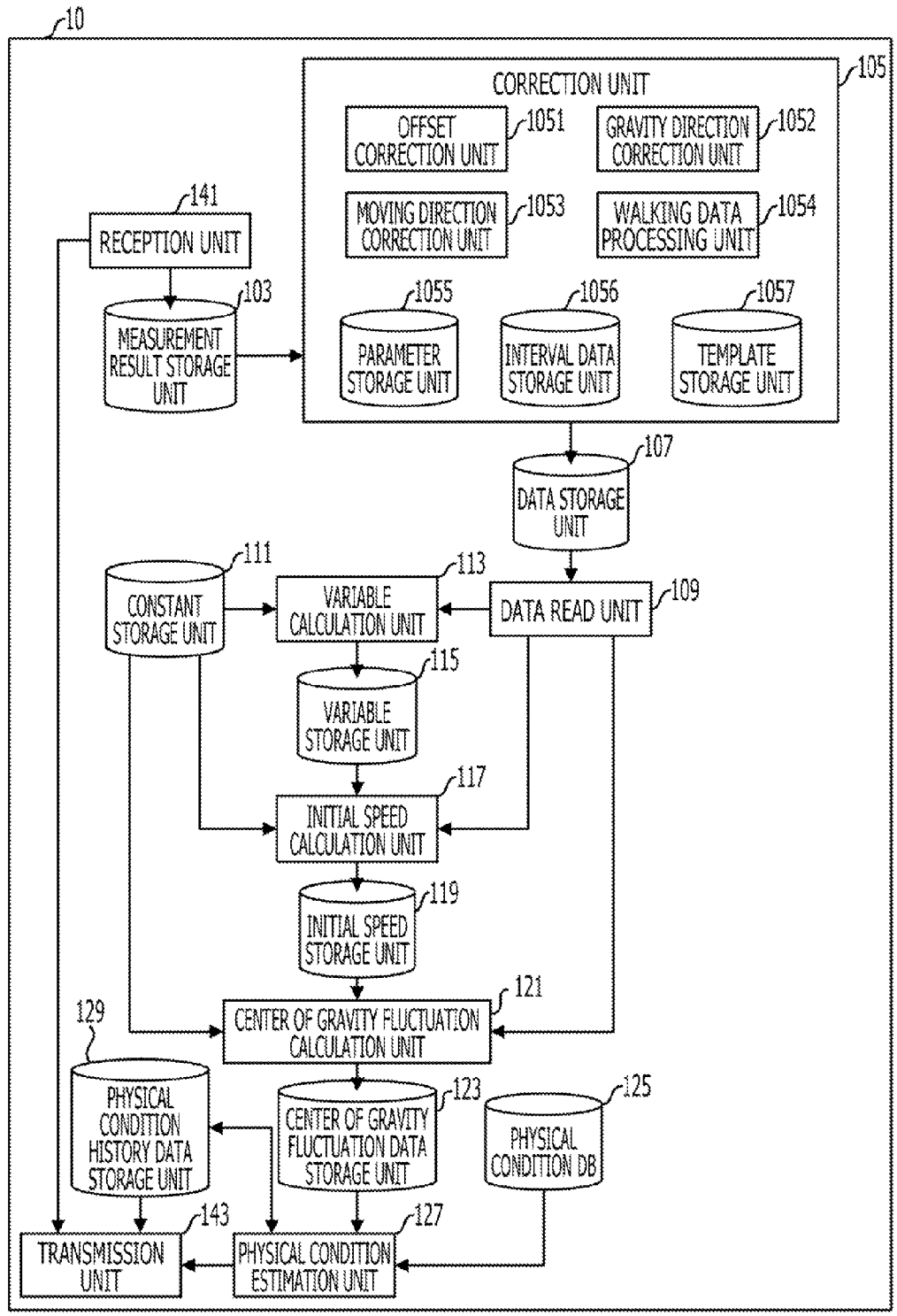
FIG. 32 is a functional block diagram of a server according to the second embodiment.

FIG. 32 is a functional block diagram of the server 10. In the client-server type system embodiment described below and illustrated in FIG. 32, similar components as illustrated in FIG. 1 are assigned the same reference numerals. The server 10 includes a reception unit 141, a measurement result storage unit 103, a correction unit 105, a data storage unit 107, a data read unit 109, a constant storage unit 111, a variable calculation unit 113, a variable storage unit 115, an initial speed calculation unit 117, an initial speed storage unit 119, a center of gravity fluctuation calculation unit 121, a center of gravity fluctuation data storage unit 123, a physical condition DB 125, a physical condition estimation unit 127, a physical condition history data storage unit 129, and a transmission unit 143. Among the above components, the following components are substantially the same as those according to the first embodiment: the measurement result storage unit 103, the correction unit 105, the data storage unit 107, the data read unit 109, the constant storage unit 111, the variable calculation unit 113, the variable storage unit 115, the initial speed calculation unit 117, the initial speed storage unit 119, the center of gravity fluctuation calculation unit 121, the center of gravity fluctuation data storage unit 123, the physical condition DB 125, the physical condition estimation unit 127, and the physical condition history data storage unit 129.

The reception unit 141 sequentially receives acceleration values transmitted from the terminal 20 with a sensor through the network 50 and stores the received values in the measurement result storage unit 103. Moreover, when the reception unit 141 receives a physical condition information transmission request, the reception unit 141 transmits the physical condition information to the transmission unit 143. The transmission unit 143 reads physical condition of the user to whom the terminal 20 with a sensor is attached from the physical condition history data storage unit 129 when the transmission unit 143 receives the physical condition information transmission request from the reception unit 141. The physical condition history data and physical condition management data are stored in the physical condition history data storage unit 129 through the above-described processing. The transmission unit 143 transmits data that indicates the user's physical condition to the in-vehicle equipment 30, for example, through an IP address included in the physical information transmission request.

The in-vehicle equipment 30 includes a reception unit 301, a proximity detection unit 303, and an output unit 305. When the reception unit 301 receives data that indicates the user's physical condition from the server 10, the reception unit 301 outputs the user's physical condition to the output unit 305. When the output unit 305 receives the data from the reception unit 301, the output unit 305 displays the data on the display device or notifies the data through an audio, for example.

For example, if a user's physical condition is a "poor physical condition" when the user is getting in a vehicle, the in-vehicle equipment 30 may notify the user not to drive. Moreover, when the user is under the influence of alcohol, the in-vehicle equipment 30 may alert the user or may not start the engine.

Here, the system configuration with the in-vehicle equipment 30 is described. However, a system configuration with a device other than the in-vehicle equipment 30 may be used.

Embodiments of the disclosed technology are described above; however, the embodiments of the technology are not limited to those described above. For example, the functional block diagrams of the mobile terminal 1, the server 10, the terminal 20 with a sensor, and the in-vehicle equipment 30 do not necessarily correspond to actual program module configurations. The configuration of the data storage unit is just one example. Moreover, the order of processing may be replaced in the processing flow as long as the processing result does not change. Furthermore, the processing may be executed in parallel.

Figure 35:
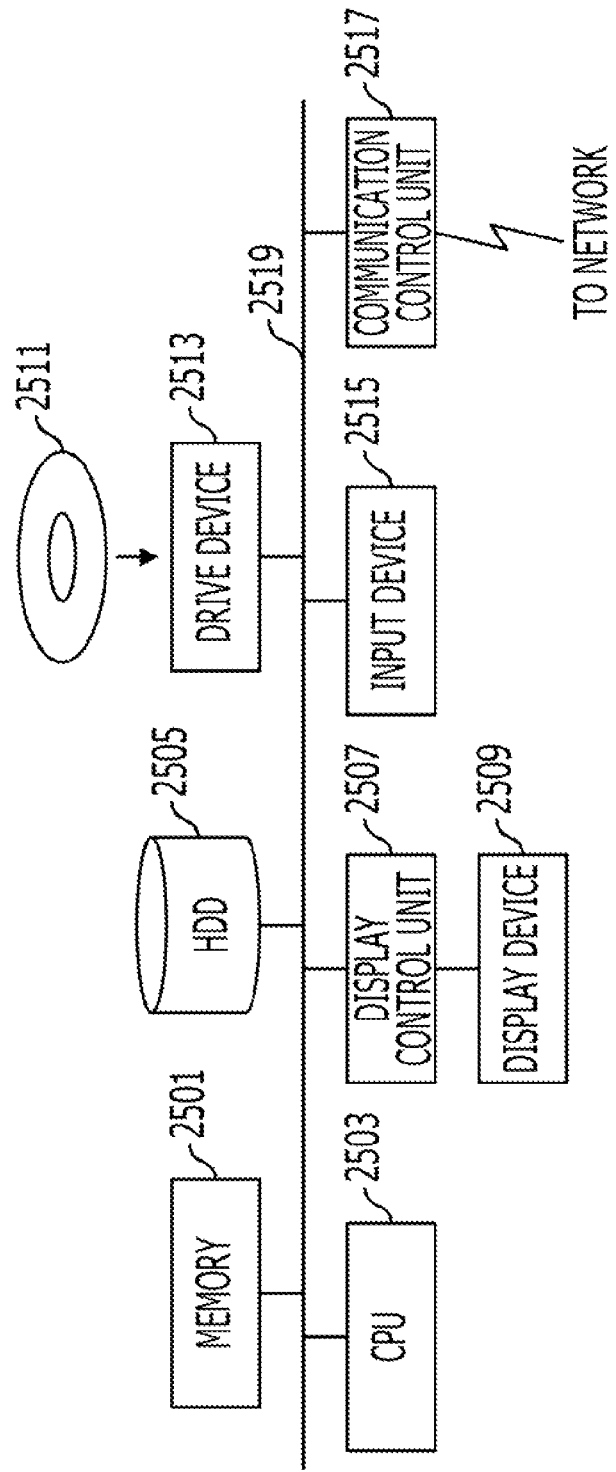
FIG. 35 is a functional block diagram of a computer.

The above-described mobile terminal 1, server 10, terminal 20 with a sensor, and the in-vehicle equipment 30 may be computer devices and as illustrated in FIG. 35, the following components may be coupled to the computer devices through a bus 2519. The components include a memory 2501, a CPU 2503, a hard disk drive (HDD) 2505, a display control unit 2507 that is coupled to a display device 2509, a drive device 2513 for a removable disk 2511, an input device 2515, and a communication control unit 2517 to couple to a network. An operating system (OS) and application programs to execute processing according to the embodiment are stored in the HDD 2505 and are read from the HDD 2505 to the memory 2501 when the CPU 2503 executes the OS and the application programs. The CPU 2503 controls the display control unit 2507, the communication unit 2517 and the drive device 2513 so as to make the components conduct certain processing according to a processing content of an application program. Moreover, data being processed is mainly stored in the memory 2501, however the data being processed may be stored in the HDD 2505. According to the embodiment, the application programs to conduct the above-described processing are stored in and distributed through a computer-readable removable disk 2511 and installed from the drive device 2513 in the HDD 2505. The application programs may be installed in the HDD 2505 through a network such as the Internet or the communication control unit 2517. The above-described computer device achieves the above-described various functions through organic cooperation between hardware such as the CPU 2503 and the memory 2501, and the programs such as the OS and the application programs.

When the mobile terminal 1 and the terminal 20 with a sensor are mobile phones, the mobile phone does not include the HDD2505 and the drive device 2513. In this case, the mobile phone includes a flash memory and a storage medium interface instead. Moreover, the mobile terminal 1 and the terminal 20 with a sensor may not include a display control unit 2507 and a display device 2509.

Hereinafter, the embodiments of the disclosure will be summarized.

Figure 33:
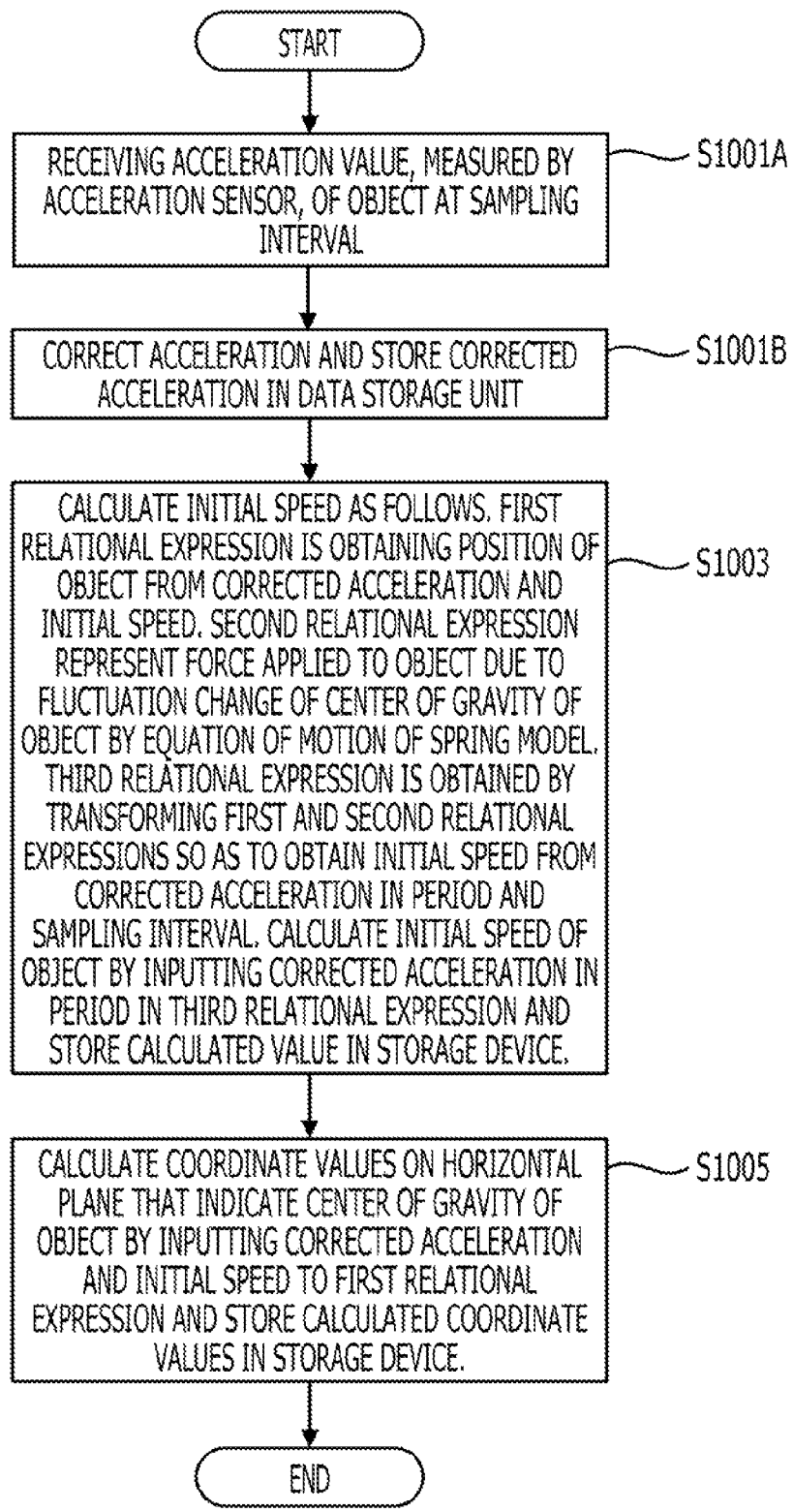
FIG. 33 is a processing flow of an information processing method according to the first embodiment.

The information processing method according to the first embodiment includes the following operations:

(A1) Receiving an acceleration value, measured by an acceleration sensor, of an object at a sampling interval (FIG. 33: S1001A)

(A2) Applying a correction to the received acceleration value and storing the corrected acceleration value in a data storage unit (FIG. 33: S1001B)

(B) Calculating an initial speed of the object by the following manner and storing the calculated result in the storage device. A first relational expression is obtaining a position of the object from the corrected acceleration and the initial speed. A second relational expression represents force applied to the object due to a change of a center of gravity of the object as a motion equation of a spring model. A third relational expression is obtained by transforming the first relational expression and the second relational expression so as to obtain the initial speed from the corrected acceleration in a period and a sampling interval. The corrected acceleration value of a period is inputted to the third relational expression to calculate the initial speed of the object. (FIG. 33: S1003)

(C) Calculating coordinate values over a horizontal plane that indicates a center of gravity of the object by inputting the corrected acceleration value and the calculated initial speed to the first relational expression and storing the calculated coordinate values in the storage device. (FIG. 33: S1005)

Introducing the third relational expression additionally as described above may calculate coordinate values on a horizontal plane that indicate a center of gravity of an object with high accuracy based on acceleration measured by the acceleration sensor even if the object does not stand still at the start of measurement. Furthermore, fluctuation of the center of gravity may be estimated from coordinate values in time series.

The above-described object may be a human body. A state identification operation may be further included in the first embodiment to identify a state of human body by using coordinate values stored in the storage device. Accordingly, a state of the human body may be obtained.

The above-described state identification operation may further include the following operations:

(A) Dividing the horizontal plane into regions with a certain angle respectively by a straight line that passes through a center point among columns of points over the horizontal plane that are represented by the coordinate values stored in the storage device.

(B) Identifying, for each of the regions, a first point where a distance from the center point is substantially the maximum and that is represented by coordinate values, converting the coordinate values of the first point into coordinate values in which the center point is assumed to be an original point, and storing the converted coordinate values in the storage device.

(C) Identifying a human body state candidate that is calculated from the coordinate values of the first point stored in the storage device and a second point by using a state database that stores coordinate values of a second point in each of the regions corresponding to each of the human body state candidates and that a distance from the human body state candidate to all of the regions is a substantially minimum.

Through the above-described operations, a human body state candidate that is closer to a current state may be identified with high accuracy from human body state candidates provided beforehand.

The above-described object may be a human being, for example. The above-described correction operation may include the following two operations. One operation is transforming a template stored in a template storage unit storing the template that indicates standard acceleration while the human being is walking so that the template is aligned with a gait cycle and amplification of acceleration identified by the acceleration value measured during a period in which the human being is assumed to be walking. The other operation is removing the standard acceleration during the walking from the acceleration value measured during the period in which the human being is assumed to be walking by using the transformed template. As described above, by removing standard acceleration during walking from the acceleration measured by the acceleration sensor allows fluctuation of the center of gravity during walking to be estimated.

The above-described initial speed calculation operation may include the following operations:

Calculating a variable "K" according to the expression (17) above by using a corrected acceleration "a" in the certain period and the number of samples N calculated from the certain period and the certain sampling interval $\Delta t$ that are stored in the data storage unit.

Calculating an initial speed $v_0$ of the object according to the above expression (28) by using a corrected acceleration "a" in the certain period, the variable "K", the certain sampling interval $\Delta t$, and the number of samples N that are stored in the data storage unit Accordingly, acceleration of an object may be calculated with high accuracy.

The first embodiment may further include the following operations:

Measuring the acceleration values at the certain sampling interval Δt by the acceleration sensor and sequentially storing the measured acceleration in the measurement result storage unit.

Calculating the initial speed may include the following operations.

Sequentially reading, for each certain period, the corrected acceleration "$a_i$" (where "i" is an integer from 0 to N−1) of the number of N acceleration generated in the certain processing target period from the data storage unit, where the number of samplings in the certain period is N.

Calculating a variable K in the certain processing target period by assigning the number of N corrected acceleration "$a_i$" that are read to the above expression 17 and storing the variable K in the storage unit.

Calculating an initial speed $v_0$ of the object in the certain processing target period by assigning the number of N corrected acceleration "$a_i$" that are read and the variable "K" stored in the storage device to the above expression 28 and storing the calculated initial speed v0 in the storage device.

Figure 34:
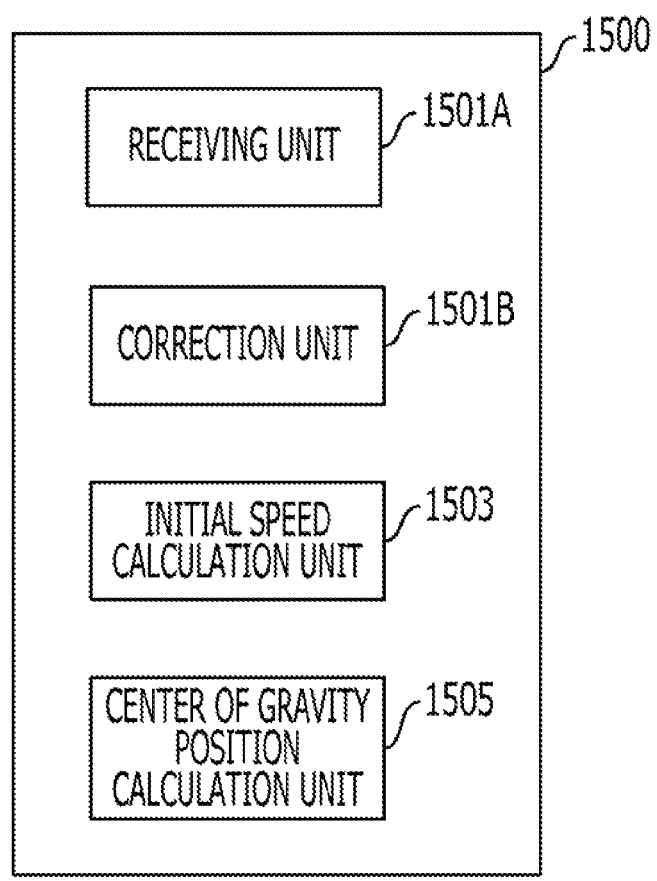
FIG. 34 is a functional block diagram of an information processing apparatus according to the second embodiment.

The information processing apparatus 1500 according to the second embodiment (FIG. 34) includes:

(A1) A receiving unit (FIG. 34: 1501A) configured to receive an acceleration value, measured by an acceleration sensor, of an object at a sampling interval.

(A2) A correction unit (FIG. 34: 1501B) configured to apply a certain correction to an acceleration value of an object measured at a certain sampling interval and to store the corrected acceleration in the data storage unit.

(B) An initial speed calculation unit (FIG. 34: 1503) configured to calculate an initial speed of an object and storing the calculated result in the storage device as follows. A first relational expression is to obtain a position of the object from acceleration and an initial speed. A second relational expression represents force applied to the object due to fluctuation of the center of gravity of the object as a motion equation of a spring model. A third relational expression is obtained by transforming the first relational expression and the second relational expression so as to obtain an initial speed from acceleration in a certain period and a certain sampling interval. The corrected acceleration value in a certain period stored in the data storage unit is assigned to the acceleration in the certain period in the third relational expression to calculate the initial speed of the object.

(C) A center of gravity position calculation unit (FIG. 34: 1505) configured to calculate coordinate values over a horizontal plane that indicates the center of gravity of the object by assigning the corrected acceleration stored in the data storage unit and the initial speed stored in the storage device and to store the calculated values in the storage device.

The second embodiment may further include an acceleration sensor configured to measure the acceleration of the object at the certain sampling interval and sequentially stores the acceleration of the object in the measurement result storage unit, wherein the correction unit may read the acceleration of the object measured in the certain period from the measurement result storage unit and apply the certain correction.

The above-described object may be a human body, for example. According to the second embodiment, a state identification unit configured as below may be further included.

to divide a horizontal plane into regions with a certain angle respectively by a straight line that passes through a center point among columns of points over the horizontal plane represented by coordinate values stored in the storage device;

to identify, for each of the regions, a first point where a distance from the center point is substantially the maximum and that is represented by the coordinate values;

to convert the coordinate values of the first point into coordinate values in which the center point is assumed to be an original point;

to store the converted coordinate values in the storage device; and to identify a human body state candidate that is calculated from the coordinate values of the first point stored in the storage device and a second point by using a state database that stores coordinate values of a second point in each of the regions corresponding to each of the human body state candidates and that a distance from the human body state candidate to all of the regions is a substantially minimum.

A program to cause a computer to execute the above-described processing may be prepared. The program may be stored, for example, in a computer readable storage medium or a storage device such as a flexible disk, a CD-ROM, an optical magnetic disk, a semiconductor memory (for example, Read Only Memory (ROM)), or a hard disk. Note that data being processed is temporarily stored in a storage device such as a Random Access Memory (RAM).

According to the embodiment, fluctuation of the center of gravity of an object may be estimated with high accuracy based on acceleration measured by the acceleration sensor regardless of whether an object stands still at the start of the measurement.

All examples and conditional language recited herein are intended for pedagogical purposes to aid the reader in understanding the invention and the concepts contributed by the inventor to furthering the art, and are to be construed as being without limitation to such specifically recited examples and conditions. Although the embodiments of the present inventions have been described in detail, it should be understood that the various changes, substitutions, and alterations could be made hereto without departing from the spirit and scope of the invention.

What is claimed is:

1. An information processing method executed by a computer including a processor, the information processing method comprising:

receiving, by the processor, an acceleration value that is measured by an acceleration sensor, of an object at a sampling interval, the acceleration sensor being provided by a mobile terminal including the processor that is configured to be attached to an object movable in three dimensions;

applying, by the processor, a correction to the received acceleration value and storing the corrected acceleration value in a storage device;

calculating, by the processor, a variable K by inputting the received acceleration values of a period to a predetermined expression;

obtaining, by the processor, a second relational expression by transforming a first relational expression using the variable K, the first relational expression defining relationships among a position of the object, the corrected acceleration values of the period, and an initial speed of the object;

calculating, by the processor, the initial speed of the object by inputting the corrected acceleration values of the period to the second relational expression so as to obtain the initial speed when the object is not standing still at a start of measurements of the acceleration values from the corrected acceleration values in the period and the sampling interval, and storing the calculated initial speed in the storage device;

calculating, by the processor, coordinate values over a horizontal plane that indicates a center of gravity of the object by inputting the corrected acceleration values and the calculated initial speed to the first relational expression and storing the calculated coordinate values in the storage device; and estimating, by the processor, a physical condition of the object by analyzing fluctuation in a center of gravity of the object obtained from the calculated coordinate values stored in the storage device, so as to detect a change in the physical condition of the object.

2. The information processing method according to claim 1, wherein the object is a user, the method further comprising:

outputting a physical condition change notification representing information on the changed physical condition.

3. The information processing method according to claim 2, wherein the estimating the physical condition of the user further comprises:

dividing the horizontal plane into regions with an angle by a straight line that passes through a center point among plural points over the horizontal plane that are represented by the calculated coordinate values;

identifying, for each of the regions, a first point where a distance from the center point is substantially a maximum and which is represented by the calculated coordinate values, converting the calculated coordinate values of the first point into coordinate values in which the center point is used as a reference point, and storing the converted coordinate values in the storage device; and identifying a user physical-condition candidate that is calculated from the calculated coordinate values of the first point and a second point by analyzing a state database that stores coordinate values of a second point in each of the regions corresponding to each of the physical-condition state candidates and that a distance from the user physical-condition candidate to all of the regions is a substantially minimum.

4. The information processing method according to claim 1, wherein the object is a user, and the correction comprises:

transforming a template stored in a template storage unit storing the template that indicates a standard acceleration value while the user is walking so that the template is aligned with a gait cycle and an amplification of acceleration identified by the acceleration value measured during a period in which the user is assumed to be walking; and subtracting the standard acceleration value during the walking from the acceleration value measured during the period in which the user is assumed to be walking by using the transformed template.

5. The information processing method according to claim 1, wherein the variable K is calculated according to the predetermined expression (where "i" indicates a sample number)

$$K = 2\left(1 - \frac{\sum_{i=2}^{N-1} a_i a_{i-1}}{\sum_{i=2}^{N-1} a_i^2}\right)$$

by using the corrected acceleration "a" in the period and the number of samples N calculated from the certain period and the certain sampling interval $\Delta t$ that is stored in the data storage unit; and calculating an initial speed $v_0$ of the object according to the second relational expression (where "j" and "i" are variables that indicate sample numbers)

$$v_0 = -\frac{\sum_{j=2}^{N}\left(a_j - (1-K)a_{j-1} + K\left(\sum_{i=0}^{j-2} a_i\right)\right)}{K(N-2)} \times \Delta t$$

by using the corrected acceleration value "a" in the period, the variable "K", the sampling interval $\Delta t$, and the number of samples N that are stored in the data storage unit.

6. The information processing method according to claim 1, further comprising:

measuring the acceleration values at the sampling interval $\Delta t$ by the acceleration sensor and sequentially storing the measured acceleration values in a measurement result storage unit;

calculating the initial speed, wherein the number of samplings in the period is N, by:

reading corrected acceleration values "$a_i$" (where i is an integer from 0 to N−1) of the number of N accelerations generated in the period to be processed from the data storage unit;

calculating the variable K in the period to be processed by assigning the number of N corrected acceleration values "$a_i$" that are read to the predetermined expression $$K = 2\left(1 - \frac{\sum_{i=2}^{N-1} a_i a_{i-1}}{\sum_{i=2}^{N-1} a_i^2}\right)$$

and storing the calculated variable K in the storage device; and calculating the initial speed $v_0$ of the object in the processing period to be processed by inputting the number of N corrected acceleration values "$a_i$" that are read and the variable "K" stored in the storage device to another expression (where "j" and "i" indicate sample numbers)

$$v_0 = -\frac{\sum_{j=2}^{N}\left(a_j - (1-K)a_{j-1} + K\left(\sum_{i=0}^{j-2} a_i\right)\right)}{K(N-2)} \times \Delta t$$

and storing the calculated initial speed $v_0$ in the storage device.

7. A non-transitory computer-readable recording medium that stores a program for causing a computer to execute a process comprising:

receiving an acceleration value that is measured by an acceleration sensor at a sampling interval, the acceleration sensor being provided by a mobile terminal configured to be attached to an object movable in three dimensions;

correcting the received acceleration value and storing the corrected acceleration value in a storage device;

calculating a variable K by inputting the received acceleration values of a period to a predetermined expression;

obtaining a second relational expression by transforming a first relational expression using the variable K, the first relational expression defining relationships among a position of the object, the corrected acceleration values of the period, and an initial speed of the object;

calculating an initial speed of the object by inputting the corrected acceleration value of the period to the second relational expression so as to obtain the initial speed when the object is not standing still at a start of measurements of the acceleration values from the corrected acceleration values in the period and the sampling interval, and storing the calculated initial speed in the storage device;

calculating coordinate values over a horizontal plane that indicates a center of gravity of the object by inputting the corrected acceleration values and the calculated initial speed to the first relational expression and storing the calculated coordinate values in the storage device, and estimating a physical condition of the object by analyzing fluctuation in a center of gravity of the object obtained from the calculated coordinate values stored in the storage device, so as to detect a change in the physical condition of the object.

8. An information processing apparatus comprising:

a processor; and a memory coupled to the processor, wherein the processor is configured:

to receive an acceleration value that is measured by an acceleration sensor at a sampling interval, the acceleration sensor provided by a mobile terminal including the processor and configured to be attached to an object movable in three dimensions;

to apply a correction to the received acceleration value and to store the corrected acceleration value in the memory;

to calculate a variable K by inputting the received acceleration values of a period to a predetermined expression;

to obtain a second relational expression by transforming a first relational expression using the variable K, the first relational expression defining relationships among a position of the object, the corrected acceleration values of the period, and an initial speed of the object;

to calculate an initial speed of the object by inputting the corrected acceleration values of the period to the second relational expression so as to obtain the initial speed when the object is not standing still at a start of measurements of the acceleration values from the corrected acceleration values and the sampling interval, and store the calculated initial speed in the memory;

to calculate coordinate values over a horizontal plane that indicates the center of gravity of the object by inputting the corrected acceleration value stored in the memory and the initial speed stored in the storage device to the first relational expression and store the calculated coordinate values in the memory; and to estimate a physical condition of the object by analyzing fluctuation in a center of gravity of the object obtained from the calculated coordinate values stored in the storage device, so as to detect change in the physical condition of the object.

9. The information processing apparatus according to claim 8, wherein the acceleration sensor measures the acceleration of the object at the sampling interval and sequentially stores the acceleration of the object in the storage device, and wherein the processor reads the acceleration values of the object measured in the period from the storage device and applies the correction.

10. The information processing apparatus according to claim 8, wherein the object is a user, and the processor is further configured:

to divide the horizontal plane into regions with an angle respectively by a straight line that passes through a center point among plural points over the horizontal plane represented by the calculated coordinate values stored;

to identify, for each of the regions, a first point where a distance from the center point is substantially a maximum and which is represented by the calculated coordinate values;

to convert the calculated coordinate values of the first point into coordinate values in which the center point is used as a reference point;

to store the converted coordinate values in the memory; and to identify a user physical-condition candidate that is calculated from the calculated coordinate values of the first point and a second point by analyzing a state database that stores coordinate values of the second point in each of the regions corresponding to each of the user physical-condition candidates and that a distance from the user physical-condition candidate to all of the regions is substantially minimum.

* * * * *